US008039613B2

(12) United States Patent
Bitner

(10) Patent No.: US 8,039,613 B2
(45) Date of Patent: Oct. 18, 2011

(54) METHODS OF PURIFYING A NUCLEIC ACID AND FORMULATION AND KIT FOR USE IN PERFORMING SUCH METHODS

(75) Inventor: Rex M. Bitner, Cedarburg, WI (US)

(73) Assignee: Promega Corporation, Madison, WI (US)

( * ) Notice: Subject to any disclaimer, the term of this patent is extended or adjusted under 35 U.S.C. 154(b) by 200 days.

(21) Appl. No.: 12/549,806

(22) Filed: Aug. 28, 2009

(65) Prior Publication Data

US 2011/0054161 A1    Mar. 3, 2011

(51) Int. Cl.
*C07H 21/00*    (2006.01)
(52) U.S. Cl. .................... 536/25.41; 536/25.42
(58) Field of Classification Search .......... None
See application file for complete search history.

(56) References Cited

U.S. PATENT DOCUMENTS

| | | | |
|---|---|---|---|
| 3,389,133 A | 6/1968 | Gutcho |
| 3,652,761 A | 3/1972 | Weetall |
| 3,897,309 A | 7/1975 | Grabner |
| 4,059,512 A | 11/1977 | Harris |
| 4,224,413 A | 9/1980 | Burbidge |
| 4,233,169 A | 11/1980 | Beall et al. |
| 4,297,337 A | 10/1981 | Mansfield et al. |
| 4,298,500 A | 11/1981 | Abbott |
| 4,395,271 A | 7/1983 | Beall et al. |
| 4,491,660 A | 1/1985 | Gendrich et al. |
| 4,523,996 A | 6/1985 | Charles et al. |
| 4,554,088 A | 11/1985 | Whitehead et al. |
| 4,659,678 A | 4/1987 | Forrest et al. |
| 4,661,260 A | 4/1987 | Kodama et al. |
| 4,661,407 A | 4/1987 | Henderson |
| 4,672,040 A | 6/1987 | Josephson |
| 4,683,202 A | 7/1987 | Mullis |
| 4,695,393 A | 9/1987 | Whitehead et al. |
| 4,699,717 A | 10/1987 | Riesner et al. |
| 4,743,545 A | 5/1988 | Torobin |
| 4,767,670 A | 8/1988 | Cox et al. |
| 4,780,423 A | 10/1988 | Bluestein et al. |
| 4,808,314 A | 2/1989 | Karplus et al. |
| 4,861,705 A | 8/1989 | Margel |
| 4,866,034 A | 9/1989 | Ribi |
| 4,885,168 A | 12/1989 | Hashimoto et al. |
| 4,921,805 A | 5/1990 | Gebeyehu et al. |
| 4,925,818 A | 5/1990 | Schneider et al. |
| 4,927,749 A | 5/1990 | Dorn |
| 4,927,750 A | 5/1990 | Dorn |
| 4,935,342 A | 6/1990 | Seligson et al. |
| 4,966,613 A | 10/1990 | Beaver |
| 5,039,559 A | 8/1991 | Sang et al. |
| 5,057,426 A | 10/1991 | Henco et al. |
| 5,059,527 A | 10/1991 | White et al. |
| 5,075,430 A | 12/1991 | Little |
| 5,076,950 A | 12/1991 | Ullman et al. |
| 5,126,239 A | 6/1992 | Livak et al. |
| 5,155,018 A | 10/1992 | Gillespie et al. |
| 5,169,535 A | 12/1992 | Adachi et al. |
| 5,234,809 A | 8/1993 | Boom et al. |
| 5,316,680 A | 5/1994 | Frechet et al. |
| 5,346,994 A | 9/1994 | Chomczynski |
| 5,389,449 A | 2/1995 | Afeyam et al. |
| 5,395,498 A | 3/1995 | Gombinsky et al. |
| 5,401,415 A | 3/1995 | Rauh et al. |
| 5,403,917 A | 4/1995 | Boos et al. |
| 5,437,983 A | 8/1995 | Watts et al. |
| 5,482,834 A | 1/1996 | Gillespie |
| 5,491,083 A | 2/1996 | Arentzen et al. |
| 5,512,439 A | 4/1996 | Hornes et al. |
| 5,523,231 A | 6/1996 | Reeve |
| 5,561,064 A | 10/1996 | Marquet et al. |
| 5,563,068 A | 10/1996 | Zhang et al. |
| 5,564,104 A | 10/1996 | Pourfarzaneh |
| 5,576,185 A | 11/1996 | Coulter et al. |
| 5,582,988 A | 12/1996 | Backus et al. |
| 5,585,236 A | 12/1996 | Bonn et al. |
| 5,589,459 A | 12/1996 | Porro |
| 5,591,628 A | 1/1997 | Baek et al. |
| 5,610,274 A | 3/1997 | Wong et al. |

(Continued)

FOREIGN PATENT DOCUMENTS

AU        707115        1/1997

(Continued)

OTHER PUBLICATIONS

Mrazek et al., *Acta Univ. Palacki. Olomuc., Fac. Med.* 142:23-28 (1999).
Lin et al., *BioTechniques*, 29:460-466 (2000).
Scott Jr. et al., *Lett. Appl. Microbiol.*, 31:95-99 (2000).
Ahn et al., *BioTechniques*, 29:466-468 (2000).
Taylor et al., *J. Chromatography A*, 890:159-166 (2000).
Abbaszadagan et al., "Detection of enteroviruses in groundwater with the [CT," Appl. Environ. Microbiol. (1993) 59(5):1318-1324.
Advertisement, Promega Corporation Nucleic Acid purification products, "Having trouble seeing how to optimize your nucleic acid purification process?" Nature Biotechnology, vol. 19, No. 5, May 2001 (9228-AD-HT).
Advertisement, Wizard® Nucleic Acid Purification Systems, Science, vol. 282, Dec. 4, 1998. (Wizard® PureFection Plasmid DNA Purification System and PolyATtract® mRNA Isolation Systems) 2 pages.

(Continued)

*Primary Examiner* — Lawrence E Crane
(74) *Attorney, Agent, or Firm* — Michael Best & Friedrich LLP

(57) ABSTRACT

A formulation containing guanidine thiocyanate together with acetamide, one or more acetamide derivatives, or a combination of acetamide and one or more acetamide derivatives is used to purify one or more nucleic acids contained in a medium. In particular, a medium containing at least one nucleic acid is combined with a binding matrix and the formulation in order to cause the at least one nucleic acid to separate from its in vivo cellular environment and to bind to the binding matrix. The binding matrix with at least one nucleic acid bound thereto then is separated from substantially the rest of the combined medium and formulation, after which the at least one nucleic acid is eluted from the binding matrix to obtain the at least one nucleic acid in a substantially purified form. If different nucleic acids are to be selectively purified from a single medium, multiple binding matrices, each compatible with a different nucleic acid, can be used.

15 Claims, 10 Drawing Sheets

U.S. PATENT DOCUMENTS

| | | | |
|---|---|---|---|
| 5,639,599 A | 6/1997 | Ryder et al. | |
| 5,652,348 A | 7/1997 | Burton et al. | |
| 5,654,141 A | 8/1997 | Mariani et al. | |
| 5,658,548 A | 8/1997 | Padhye et al. | |
| 5,660,984 A | 8/1997 | Davis et al. | |
| 5,674,997 A | 10/1997 | Woodard et al. | |
| 5,681,946 A | 10/1997 | Reeve | |
| 5,683,875 A | 11/1997 | Lichtenwalter et al. | |
| 5,693,785 A | 12/1997 | Woodard et al. | |
| 5,705,628 A | 1/1998 | Hawkins | 536/25.4 |
| 5,728,822 A | 3/1998 | Macfarlane | |
| 5,734,020 A | 3/1998 | Wong et al. | |
| 5,746,978 A | 5/1998 | Bienhaus et al. | |
| 5,747,663 A | 5/1998 | Colpan et al. | |
| 5,783,686 A | 7/1998 | Gonzalez | |
| 5,789,148 A | 8/1998 | Van Vlasselaer et al. | |
| 5,790,964 A | 8/1998 | Pourfarzaneh | |
| 5,792,651 A | 8/1998 | Colpan et al. | |
| 5,804,684 A | 9/1998 | Su et al. | |
| 5,808,041 A | 9/1998 | Padhye et al. | |
| 5,861,315 A | 1/1999 | Nakahata | |
| 5,898,071 A | 4/1999 | Hawkins | 536/25.4 |
| 5,904,848 A | 5/1999 | Wong et al. | |
| 5,945,525 A | 8/1999 | Uematsu et al. | |
| 5,973,138 A | 10/1999 | Collis et al. | |
| 5,981,235 A | 11/1999 | Shultz et al. | |
| 5,990,301 A | 11/1999 | Colpan et al. | |
| 6,027,945 A | 2/2000 | Smith et al. | 436/526 |
| 6,045,697 A | 4/2000 | Girot et al. | |
| 6,048,695 A | 4/2000 | Bradley et al. | |
| 6,051,380 A | 4/2000 | Sosnowski et al. | |
| 6,084,091 A | 7/2000 | Muller et al. | |
| 6,103,127 A | 8/2000 | Pourfarzaneh | |
| 6,117,398 A | 9/2000 | Bienhaus et al. | |
| 6,156,504 A | 12/2000 | Gocke et al. | |
| 6,180,778 B1 | 1/2001 | Bastian et al. | |
| 6,194,562 B1 | 2/2001 | Smith et al. | |
| 6,218,531 B1 | 4/2001 | Ekenberg | |
| 6,255,477 B1 | 7/2001 | Kleiber et al. | |
| 6,270,970 B1 | 8/2001 | Smith et al. | |
| 6,284,470 B1 | 9/2001 | Bitner et al. | |
| 6,310,199 B1 | 10/2001 | Smith et al. | |
| 6,344,326 B1 | 2/2002 | Nelson et al. | |
| 6,368,800 B1 | 4/2002 | Smith et al. | |
| 6,376,194 B2 | 4/2002 | Smith et al. | |
| 6,410,725 B1 | 6/2002 | Scholl et al. | |
| 6,416,671 B1 | 7/2002 | Pourfarzaneh | |
| 6,506,559 B1 | 1/2003 | Fire | |
| 6,534,262 B1 | 3/2003 | McKernan et al. | 435/6 |
| 6,613,895 B1 | 9/2003 | Gautsch et al. | |
| 6,617,108 B1 | 9/2003 | Wilson et al. | |
| 6,656,587 B2 | 12/2003 | Johnson et al. | |
| 6,658,548 B1 | 12/2003 | Kochar et al. | |
| 6,670,332 B1 | 12/2003 | Wheeler | |
| 6,673,631 B1 | 1/2004 | Tereba et al. | 436/526 |
| 6,787,307 B1 | 9/2004 | Bitner et al. | |
| 6,804,684 B2 | 10/2004 | Su | |
| 6,806,362 B2 | 10/2004 | Smith et al. | |
| 6,855,499 B1 | 2/2005 | Nargessi | 435/6 |
| 6,914,137 B2 | 7/2005 | Baker | |
| 6,919,175 B1 | 7/2005 | Bienhaus et al. | |
| 6,992,182 B1 | 1/2006 | Muller et al. | |
| 7,078,224 B1 | 7/2006 | Bitner et al. | |
| 7,208,269 B2 | 4/2007 | Bavykin | |
| 7,264,927 B2 | 9/2007 | Nargessi et al. | |
| 7,601,491 B2 | 10/2009 | Collis et al. | |
| 7,727,727 B2 | 6/2010 | Collis et al. | |
| 2002/0004111 A1 | 1/2002 | Matsubara et al. | |
| 2002/0162797 A1 | 11/2002 | Johnson et al. | |
| 2002/0165388 A1 | 11/2002 | Bavykin et al. | |
| 2003/0013112 A1 | 1/2003 | Sprenger | |
| 2003/0096366 A1 | 5/2003 | Knudsen | |
| 2003/0138828 A1 | 7/2003 | Bost et al. | |
| 2004/0018559 A1 | 1/2004 | Lau et al. | |
| 2004/0023273 A1 | 2/2004 | Puget et al. | |
| 2004/0086930 A1 | 5/2004 | Tereba et al. | |
| 2004/0137449 A1 | 7/2004 | Nargessi | |
| 2004/0180445 A1 | 9/2004 | Domanico et al. | |
| 2004/0258570 A1 | 12/2004 | Beebe et al. | |
| 2005/0059024 A1 | 3/2005 | Conrad | |
| 2005/0079535 A1 | 4/2005 | Kirchgesser et al. | |
| 2005/0214926 A1 | 9/2005 | Zielenski et al. | |
| 2005/0260625 A1 | 11/2005 | Wang | |
| 2005/0282202 A1 | 12/2005 | Brolaski et al. | |
| 2006/0240448 A1 | 10/2006 | Bitner et al. | |
| 2007/0015191 A1 | 1/2007 | Bitner et al. | |
| 2007/0087385 A1 | 4/2007 | Muller-Schulte | |
| 2007/0172855 A1 | 7/2007 | Bitner et al. | 435/6 |
| 2007/0249821 A1 | 10/2007 | Bitner et al. | |
| 2009/0088560 A1 | 4/2009 | Shen | |
| 2011/0054157 A1 | 3/2011 | Bitner et al. | |

FOREIGN PATENT DOCUMENTS

| | | |
|---|---|---|
| CA | 2223821 | 6/1996 |
| DE | 3935098 | 4/1991 |
| DE | 4307262 | 9/1994 |
| DE | 4333805 | 3/1995 |
| DE | 19512368 | 10/1996 |
| EP | 0391608 | 10/1990 |
| EP | 0581651 | 2/1994 |
| EP | 0837871 | 6/1996 |
| EP | 0741141 | 11/1996 |
| EP | 0757106 | 2/1997 |
| EP | 0875271 | 11/1998 |
| EP | 0992583 | 4/2000 |
| EP | 1479769 | 11/2004 |
| GB | 2074892 | 11/1981 |
| JP | 62151752 | 7/1987 |
| JP | 62-190466 | 8/1987 |
| JP | 62235207 | 10/1987 |
| JP | 02-289598 | 11/1990 |
| JP | 02289596 | 11/1990 |
| JP | 03-101689 | 4/1991 |
| JP | 6126635 | 5/1994 |
| JP | 07-059572 | 3/1995 |
| JP | 07235407 | 9/1995 |
| JP | 0919292 | 1/1997 |
| JP | 9327290 | 12/1997 |
| JP | 9327291 | 12/1997 |
| JP | 10316696 | 12/1998 |
| JP | 11-92494 | 4/1999 |
| WO | WO 83/03363 | 10/1983 |
| WO | WO 86/05815 | 10/1986 |
| WO | WO 91/05606 | 5/1991 |
| WO | WO 91/12079 | 8/1991 |
| WO | WO 93/10162 | 5/1993 |
| WO | WO 95/06652 | 3/1995 |
| WO | WO 95/21177 | 8/1995 |
| WO | WO 95/21179 | 8/1995 |
| WO | WO 96/03653 | 2/1996 |
| WO | WO 96/09379 | 3/1996 |
| WO | WO 96/16186 | 5/1996 |
| WO | WO 96/31781 | 10/1996 |
| WO | WO 96/36706 | 11/1996 |
| WO | WO 96/41811 | 12/1996 |
| WO | WO 97/08547 | 3/1997 |
| WO | WO 97/29825 | 8/1997 |
| WO | WO 97/30152 | 8/1997 |
| WO | WO 97/32893 | 9/1997 |
| WO | WO 98/31461 | 7/1998 |
| WO | WO 98/31840 | 7/1998 |
| WO | WO 99/36359 | 7/1999 |
| WO | WO 99/54340 | 10/1999 |
| WO | WO 00/69872 | 11/2000 |
| WO | WO 00/70040 | 11/2000 |
| WO | WO 00/70041 | 11/2000 |
| WO | WO 01/62976 | 8/2001 |
| WO | WO 02/09125 | 1/2002 |
| WO | WO 02/38758 | 5/2002 |
| WO | WO 02/066993 | 8/2002 |
| WO | WO 02/087871 | 11/2002 |
| WO | WO 03/033739 | 4/2003 |
| WO | WO 03/040687 | 5/2003 |
| WO | WO 03/046146 | 6/2003 |
| WO | WO 03/082892 | 10/2003 |
| WO | WO 2004/096984 | 11/2004 |
| WO | WO 2004/108741 | 12/2004 |

| WO | WO 2004/108925 | 12/2004 |
| --- | --- | --- |
| WO | WO 2005/052581 | 6/2005 |
| WO | WO 2007/005613 | 1/2007 |
| WO | WO 2007/070381 | 6/2007 |
| WO | WO 2007/103485 | 9/2007 |
| WO | WO 2008/112015 | 9/2008 |
| WO | WO 2008/127356 | 10/2008 |
| WO | WO 2011/026027 | 3/2011 |
| WO | WO 2011/026028 | 3/2011 |

OTHER PUBLICATIONS

Advertisement, Wizard® PureFection Plasmid DNA Purification System, Science, vol. 282, Oct. 30, 1998.
Ahn, S.C. et al., "Rapid mini-scale plasmid isolation for DNA sequencing and restriction mapping," BioTechniques (2000) 29:466-468.
Aida, Y. et al., "Removal of endotoxin from protein solutions by phase separation using Triton X-114," J. Immunol. Methods (1990) 132:191-195.
Anspach, F.B. "High performance liquid affinity chromatography with phenylboronic acid, benzamidine, tri-L-alanine, and concanavalin A immobilized on 3-isothiocyanatopropyltriethoxysilane-activated nonporous monodisperse silicas," Anal. Biochem. (1989) 1797:171-181.
Anspach, F.B. et al., "Removal of endotoxins by affinity sorbents," J. Chrom. A (1995) 711:81-92.
Astell et al., "Thermal elution of complementary sequences of nucleic acids from cellulose columns with covalently attached oligonucleotides of known length and sequence," J. Biol. Chem. (1971) 248:1944-1946.
Ausubel et al., eds. Chapter 2 (DNA) and Chapter 4 (RNA) of Current Protocols in Molecular Biology, Wiley-Interscience, New York (1993).
Ausubel et al., eds., Chapter 2 (DNA) and Chapter 4 (RNA) of Current Protocols in Molecular Biology, Wiley-Interscience, New York (1987).
Ausubel, F.M. et al., Short Protocols in Molecular Biology, Third Edition, John Wiley & Sons, Inc. (1997) p. 9-52.
Biocontrol Network, "Perma-guard diatomaceous earth," http://www.biconet.com (1998) 5 pages.
Bischoff, R. et al., "Chemically synthesized hydrophobic anion-exchange high-performance liquid chromatography supports used for oligonucleotide resolution by mixed mode chromatography," J. Chromatog. (1983) 270:117-126.
Bischoff, R. et al., "Nucleic acid resolution by mixed-mode chromatography," J. Chromatog (1984) 296:329-337.
Bitner R. et al., "Automation of DNA extraction from food and plants using MagneSil™ paramagnetic particles," Proceedings of SPIE.V. 4264 (2001). Submitted Jan. 2001, Genomics & Proteomics Technologies, pp. 9-16.
Bitner, R et al., "Use of MagneSil paramagnetic particles for plasmid purification, PCR cleanup and purification of dideoxy and big dye DNA sequencing reactions," Advances in Nucleic Acid and Protein Analyses, Manipulation and Sequencing, Proceedings of SPIE (2000) 3926:126-133.
Boom, R. et al., "Rapid and simple method for purification of nucleic acids," J. Clin. Microbiol. (1990) 28:495-503.
Brinker, C.J. et al., "Sol gel science: the physics and chemistry of sol gel processing," Academic Press Inc. (1990).
Brisco, P. et al., "Use of a 96 well format for small scale mRNA isolation and cDNA synthesis,"Promega Notes Magazine, No. 52, pp. 8-13 (1995).
Brown et al., "Anion-cation separations on a mixed bed alumina-sillica column," J. Chromatog. (1989) , 466(1):291-300.
Brummelkamp et al., "A system for stable expression of short interfering RNAs in mammalian cells," Science (2002) 296:550-553.
Burke, P., "PolyATtract® mRNA isolation systems," Promega Notes Magazine, No. 56, pp. 27-29 (1996).
Caplen, N. et al., "Specific inhibition of gene expression by small double-stranded RNAs in invertebrate and vertebrate systems," Proc. Natl. Acad. Sci. USA (2001) 98(17):9742-9747.
Chen et al., Anal. Biochem. (1980) 101:339-341.
Controlled Pore Glass Products, CPG, Inc., Online, http://www.cpg-biotech.com (2002).
Cotten, M. et al., "Lipopolysaccharide is a frequent contaminant of plasmid DNA preparations and can be toxic to primary human cells in the presence of adenovirus," Gene Therapy (1994) 1:239-246.
Creswell, D., et al., "Increasing yield with the Wizard® PureFection Plasmid DNA Purification System," Promega Notes Magazine, No. 73 pp. 17-19 (1999).
Crowther, J.B. et al., "High-performance liquid chromatographic separation of oligonucleotides and other nucleic acid constituents on multifunctional stationary phases," J. Chromatog. (1983) 282:619-628.
Davies, M.J. et al., "Isolation of plasmid DNA using magnetite as a solid-phase adsorbent," Anal. Biochem. (1998) 262:92-94.
Davis, H.L. et al., "Direct gene transfer into skeletal muscle in vivo: factors affecting efficiency of transfer and stability of expression," Human Gene Ther. (1993) 4:151-159.
Edwardson, P.A.D. et al, "Separation and purification of oligonucleotides using a new bonded-phase packing material," J. Chromatog. (1991) 545:79-89.
Elbashir, S.M. et al., "Duplexes of 21-nucleotide RNAs mediate RNA interference in cultured mammalian cells," Nature (2001) 411:494-498.
Elbashir, S.M. et al., "Functional anatomy of siRNAs for mediating efficient RNAi in drosophila melanogaster embryo lysate," EMBO J. (2001) 20(23):6877-6888.
Elbashir, S.M. et al., "RNA interference is mediated by 21- and 22-nucleotide RNAs," Genes & Dev. (2001) 15:188-200.
Ennifar, E. et al., "A crystallographic study of the binding of 13 metal ions to two related RNA duplexes," Nucl. Acids Res. (2003) 31(10):2671-2682.
Figueroa, A. et al., "High-performance immobilized-metal affinity chromatography of proteins on iminodiacetic acid silica-based bonded phases," J. Chromatog. (1986) 371:335-352.
Floyd, T.R. et al., "Mixed-mode hydrophobic ion exchange for the separation of oligonucleotides and DNA fragments using HPLC," Analytical Biochemistry (1986) 154:570-577.
Ford, The University of Edinburgh, U.K., Welcome to the Biology Teaching Organisation, see glossary definition of "lysis," web published with last update of Nov. 19, 1997, originally published at http://www.icmb.edinburgh.ac.uk.bto/glossary (site is archived and is not presently active) 3 pages.
Franklin, R.M., "Purification and properties of the replicative intermediate of the RNA bacteriophage R17," Biochem. (1966) 55:1504-1511.
Gibco BRL Products & References Guide 1997/1998, Life Technologies, "Aces 2.0+ human DNA quantitation system," pp. 19-28.
Gjerde, D.T. et al., Ion chromatography, Ch. 3, Dr. Alfred Hothig Verlag Heidelberg (1987) 2nd Edition, 3 pages.
Goldsborough, M.D. et al., "High purity plasmid DNA from anion exchange chromatography," Focus (1998) 20(3):68-69.
Greenspoon, S. et al., "Robotic extraction of mock sexual assault samples using the biomek 2000 and the DNA IQ system," Profiles in DNA (2002) 5(1).
Harkins, W.D. et al., Proceedings of the National Academy of Sciences of the United States of America (1916) 2(10):599-600, http://www.jstor.org/stable/83481.
Harris, A.B., "Solvent pH and salt concentration in rapid resolution of nucleic acid bases on cellulose layers," Biochem. Biophys. Acta (1967) 145:520-522.
Hawkins, T.L. et al., "DNA purification and isolation using a solid-phase," Nucl. Acids. Res. (1994) 22(21):4543-4544.
Hirabayashi, J., "Applied slalom chromatography improved DNA separation by the use of columns developed for reversed-phase chromatography," J. Chrom. (1996) 722:135-142.
Holen, T. et al., "Positional effects of short interfering RNAs targeting the human coagulation trigger tissue factor," Nucl. Acids Res. (2002) 30(8):1757-1766.
http://seq.veastgenome.org/vector_descrip/COMPLETE/PUC18.seq.htm, downloaded Nov. 13, 2008.
Huber, C.G. et al., "High-resolution liquid chromatography of DNA fragments on non-porous poly(styrenedivinylbenzene) particles," Nucl. Acids. Res. (1993) 21(5):1061-1066.

Jost, W. et al., "Application of a weekly basic dimethylamino-modified silica ion exchanger to the separation of oligonucleotides," J. Chromatog. (1979) 185:403-412.

Karplus, T.E. et al., "A new method for reduction of endotoxin contamination from protein solutions," J. Immunol. Met. (1987) 105:211-220.

Kephart, D., "Rapid isolation of RNA from small quantities of human whole blood for use in RT-PCR analysis," *Promega Notes Magazine*, No. 62 pp. 11-16 (1997).

Keys et al., "The use of cellulose phosphate in the extraction of free nucleotides from plant tissue," Proceedings of the Biochemical Society (1969) pp. 16-17.

Kieft, J.S. et al., "Solution structure of a metal-binding site in the major groove of RNA complexed with cobalt (III) hexammine," Structure (1997) 5(5):713-721.

Kimpton et al., "Validation of highly discriminating multiplex short tandem repeat amplification systems for individual identification," Electrophoresis (1996) 17(8):1283-1293.

Kirk-Othmer Encyclopedia of Chemical Technology, vol. 21, 4th Edition, Mary Howe-Grant, Ed., John Wiley & Sons (1997) pp. 1020-1023.

Kirk-Othmer Encyclopedia of Chemical Technology, vol. 6, 4th ed., John Wiley & Sons (1993) pp. 773-775.

Kleiber, J. et al., "Magnetic particles and their use for isolation of biological materials," Gen. Offen. (1996) Database CAS online AN 126:86772 9 pp. Abstract, 1 page.

Kothari et al., "RNA fractionation on modified celluloses," J. Chromatog. (1972) 73:449-462.

Kotsopoulos, S.K. et al., "Isolation of 3.5-KB fragments on magnetic solid supports," BioTechniques (1996) 20:198-200.

Krizova, J. et al., "Magnetic hydrophilic methacrylate-based polymer microspheres for genomic DNA isolation," J. Chromatog. A (2005) 1064:247-253.

Lepinski, M., "Tips for working with RNA and troubleshooting downstream applications," *Promega Notes Magazine*, No. 63 pp. 17-20 (1997).

Levison, P.R. et al., "New approaches to the isolation of DNA by ion-exchange chromatography," J. Chromat. (1998) 827(2):337-344.

Levison, P.R. et al., "Recent developments of magnetic beads for use in nucleic acid purification," J. Chromatography A (1998) 816:107-111.

Lin, Z. et al., "Protocol for genomic DNA preparation from fresh or frozen serum for PCR amplification," BioTechniques (2000) 29:460-466.

Little, E.L. et al., "Sequential multimodal elution for pseudomultidimensional liquid chromatography on a single column," Anal. Chem. (1991) 63:33-44.

Liu, S. et al., "Removal of endotoxin from recombinant protein preparations," Clin. Biochem. (1997) 30(6):455-463.

Livage, J. et al. "Encapsulation of biomolecules in silica gels," J. Phys.: Condens. Matter (2001) 13:R673-691.

Maa, Y.F. et al., "Rapid high-performance liquid chromatography of nucleic acids with polystyrene-based micropellicular anion exchangers," J. Chromatog. (1990) 508:61-73.

Macherey-Nagel, homepage on the Internet on Jun. 12, 1998 at http://www.machrey-nagel.com, 3 pages.

Makowski et al., "Amplification of guthrie card DNA: effect of guanidine thiocyanate on binding of nature whole blood PCR inhibitors," J. Clin. Lab. Anal. (1997) 11:87-93.

Manthorpe, M. et al., "Gene therapy by intramuscular injection of plasmid DNA: studies on firefly luciferase gene expression in mice," Human Gene Therapy (1993) 4:419-431.

Mariani et al., "Development of novel, rapid processing protocol for polymerase chain reaction-based detection of bacterial infections in synovial fluids" Mol. Biotech. (1995) 4(3):227-237.

Marko, M.A. et al., "A procedure for the large-scale isolation of highly purified plasmic DNA using alkaline extraction and binding to glass powder," Anal. Biochem. (1982) 121:382-287.

Marvin, H.J.P. et al., "Release of outer membrane fragments from wild-type *Escherichia coli* and from several *E coli lipopolysaccharide* mutants by EDTA and heat shock treatments," J. Bacter. (1989) 171(10):5262-5267.

Matsubara et al., "Dried blood spot on filter paper as a source of mRNA," Nucl. Acids Res. (1992) 20(8):1998.

Matsubara et al., Wizard Minipreps Dna Purification Systems, Promega Corporation (Dec. 1994) 1-4.

McCormick, R.M. et al., "A solid-phase extraction procedure for DNA purification," Anal. Biochem. (1989) 181:66-74.

McElroy et al., "QSAR and classification of murine and human soluble epoxide hydrolase inhibition by urea-like compounds," J. Med. Chem. (2003) 46(6):1066-1080.

McLaughlin, L., "Mixed-mode chromatography of nucleic acids," Chem. Rev. (1989) 89:309-319.

Melzak, K.A. et al., "Driving forces for DNA adsorption to silica in perchlorate solutions," J. Colloid Interface Sci. (1996) 181:635-644.

Molvig, J. et al., "Removal of endotoxin from culture media by a polymyxin B sepharose column," Scand. J. Immunol. (1987) 26:611-619.

Montbriand, P.M. et al., "Improved method for the removal of endotoxin from DNA," J. Biotech. (1996) 44:43-46.

Morrison, D.C. et al., "Endotoxin and disease mechanisms," Ann. Rev. Med. (1987) 38:417-432.

Mrazek, F. et al., "Processing of MRNA from human leukocytes by biomagnetical separation: comparison with current methods of RNA isolation," Acta Univ. Palacki. Olomuc. Fac. Med. (1999) 142:23-28.

Murphy, J.C. et al., "RNA isolation and fractionation with compaction agents," Anal. Biochem. (2001) 295:143-148.

Neri, B.P., et al., "Transferring automation for large-scale development and production of invader SNP assays," Abstract, BIOS (2000) 2 pages.

Northrop, D.M. et al., "Preparation and evaluation of a bimodal size-exclusion chromatography column containing a mixture of two silicas of different pore diameter," Anal. Chem. (1991) 63:1350-1354.

Osorio, C.R. et al., "Characterization of the 23S and 5S rRNA genes and 23S-5S intergenic spacer region (ITS-2) of photobacterium damselae," Dis. Squat. Org. (2004) 61:33-39.

PerSeptive Diagnostics Product Guide for BioMag® MINI-PREP DNA Purification Kit (Catalog No. 8-MB4008K) Feb. 27, 1995 (4 pages).

Pourfarzaneh et al., "The use of magnetizable particles in solid phase immunoassay," Methods of Biochem. Anal. (1982) 28:267-295.

Promega Corporation—1994-95 Biologic Research Products Catalog, front cover, table of contents, pp. 155-157 (1994) PolyATtract® mRNA Isolation Systems, PolyATtract® System 1000 Magnetic Separation Stand & MagneSphere™ Technology Magnetic Separation Stand, 5 pages.

Promega Corporation—"Material Safety Data Sheet: Wizard SV96 Neutralization Solution" http://www.promega.com/msds/uk/ukmsds\A148.htm, (Jul. 3, 2002) *Box 2 (composition/data on components):guanidinium chloride*, 1-5 pages.

Promega Corporation—"Wizard SV96 Plasmid DNA Purification System" (1999) Retrieved from the Internet on Sep. 5, 2007 (http://www.promega.co.jp/jp/jp_tech/j_manuals/wsv96.pdf) pp. 1-9.

Promega Corporation—"Frequently asked questions of Promega's Technical Services Department," *Promega Notes*, No. 71, pp. 24-26 (1999).

Promega Corporation—1990-91 Product Catalogue, front and back cover, pp. 121-122 (1990) (PolyATtract™ mRNA Isolation Systems) 4 pages.

Promega Corporation—1991-92 Product Catalogue, front cover, first page of table of contents, pp. 192 and 348 (1991) (PolyATtract™ mRNA Isolation Systems & MagneSphere™ Technology Magnetic Separation Stand) 4 pages.

Promega Corporation—1992-93 Biologic Research Products Catalogue, front and back cover, first page of table of contents, pp. 161-163 (1992) (PolyATtract® mRNA Isolation Systems, PolyATtract® System 1000 Magnetic Separation Stand & MagneSphere™ Technology Magnetic Separation Stand) 6 pages.

Promega Corporation—1993-94 Product Catalog, front and back cover, first page of table of contents, pp. 149-151 (1993) (PolyATtract® mRNA Isolation Systems, PolyATtract® System 1000 Magnetic Separation Stand & MagneSphere™ Technology Magnetic Separation Stand) 5 pages.

Promega Corporation—1996 Biologic Research Products Catalog, front cover, table of contents, pp. 158-161 (1995) (PolyATtract® mRNA Isolation Systems, PolyATtract® System 1000 Magnetic Separation Stan, PolyATtract® Series 9600™ Multi-Magnet & MagneSphere™ Technology Magnetic Separation Stand) 6 pages.

Promega Corporation—1997 Biologic Research Products Catalog, front cover, table of contents, pp. 187-188 (1996) (PolyATtract® mRNA Isolation Systems, PolyATtract® System 1000 Magnetic Separation Stand, PolyATtract® Series 9600™ Multi-Magnet & MagneSphere™ Technology Magnetic Separation Stand) 5 pages.

Promega Corporation—1998 Biologic Research Products Catalog, cover and pp. 182-183 and 199-200, 5 pages.

Promega Corporation—1998 Biologic Research Products Catalog, front cover, table of contents, pp. 196-200 (1997) (PolyATtract® mRNA Isolation Systems, PolyATtract® System 1000 Magnetic Separation Stand, PolyATtract® Series 9600™ Multi-Magnet & MagneSphere™ Technology Magnetic Separation Stand), 7 pages.

Promega Corporation—1999 Life Science Catalog, front cover, table of contents, pp. 9.4, 9.19-9.22 and 10.17 (1998) (Wizard® PureFection Plasmid DNA Purification System, PolyATtract® mRNA Isolation Systems, PolyATtract® System 1000 Magnetic Separation Stand, PolyATtract® Series 9600™ Multi-Magnet & MagneSphere™ Technology Magnetic Separation Stand), 8 pages.

Promega Corporation—2000 Life Science Catalog, front cover, table of contents, pp. 2.4 and 2.12-2.14 (1999) (Wizard PureFection Plasmid DNA Purification System, PolyATtract mRNA Isolation Systems, PolyATtract System 1000 Magnetic Separation Stand, PolyATtract Series 9600 Multi-Magnet and MagneSphere Technology Magnetic Separation Stand), 6 pages.

Promega Corporation—Higher Throughput Solutions Brochure, BR094, (Jun. 2000) 6 pages.

Promega Corporation—MagneSphere® Magnetic Separation Products Technical Bulletin, TB246 (Nov. 1996) 1-10.

Promega Corporation—MagneSphere® Magnetic Separation Products Technical Bulletin, TB246 (revised Mar. 2000) 1-12.

Promega Corporation—Nucleic Acid Purification Systems Brochure, BR081 (Feb. 1999) 11 pages.

Promega Corporation—PolyATtract® mRNA Isolation System Technical Manual, TM021 (Revised Feb. 2000) 1-12.

Promega Corporation—PolyATtract® mRNA Isolation System Technical Manual, TM021 (Revised Apr. 1995)1-11.

Promega Corporation—PolyATtract® mRNA Isolation System Technical Manual, TM021 (Revised May 2001) 1-12.

Promega Corporation—PolyATtract® mRNA Isolation System Technical Manual, TM021 (Revised Aug. 1998) 1-16.

Promega Corporation—PolyATtract® System 1000 Technical Manual, TM228 (Dec. 1992) 1-19.

Promega Corporation—PolyATtract® System 1000 Technical Manual, TM228 (Revised May 2001) 1-19.

Promega Corporation—PolyATtract® System 1000 Technical Manual, TM228 (Revised Dec. 1999) 1-24.

Promega Corporation—PolyATtract® System 1000 Technical Manual, TM228 (Revised Feb. 2000) 1-23.

Promega Corporation—PolyATtract® System 1000 Technical Manual, TM228 (Revised Feb. 1997) 1-19.

Promega Corporation—PolyATtract® System 1000 Technical Manual, TM228 (Revised Mar. 1995) 1-18.

Promega Corporation—PolyATtract® System 1000 Technical Manual, TM228 (Revised Apr. 1999) 1-23.

Promega Corporation—PolyATtract® System 1000 Technical Manual, TM228 (Revised Jun. 1997) 1-19.

Promega Corporation—PolyATtract® System 1000 Technical Manual, TM228 (Revised Jun. 1998) 1-23.

Promega Corporation—Technical Bulletin No. 202, "Wizard Plus Series 9600 DNA Purification System" (Sep. 1998) 18 pages.

Promega Corporation—Technical Bulletin No. 225, "Wizard Plus SV Minipreps DNA Purification System" (Sep. 1999) 14 pages.

Promega Corporation—Technical Bulletin No. 48, "SV Total RNA Isolation System" (1998), 28 pages.

Promega Corporation—Wizard ® MagneSil™ Plasmid Purification System, TB286 (Nov. 2001) pp. 1-12.

Promega Corporation—Wizard MagneSil Tfx™ System, Technical Bulleting TB314, first printing (Oct. 2002) pp. 1-9.

Promega Corporation—Wizard® MagneSil™ Plasmid Purification System, Technical Bulletin TB286, First Printing (Feb. 2001) pp. 1-11.

Promega Corporation— Wizard® Magnetic DNA Purification System for Food Technical Bulletin, TB284 (Aug. 2000) (PolyATtract® System 1000 Magnetic Separation Stand, Cat. #Z5410), pp. 1-11.

Promega Corporation—Wizard® Magnetic DNA Purification System for Food Technical Bulletin, TB284 (Revised Mar. 2001) (PolyATtract® System 1000 Magnetic Separation Stand, Cat. #Z5410), pp. 1-13.

Promega Corporation—Wizard® Magnetic DNA Purification System for Food Technical Bulletin, TB284 (Revised May 2001) (PolyATtract® System 1000 Magnetic Separation Stand, Cat. #Z5410), pp. 1-14.

Promega Corporation— Wizard® PureFection Plasmid DNA Purification Brochure, BR076 (Feb. 1999), pp. 1-9.

Promega Corporation—Wizard® PureFection Plasmid DNA Purification System Technical Bulletin, TB259 (Oct. 1998) pp. 1-14.

Promega Corporation—Wizard® PureFection Plasmid DNA Purification System Technical Bulletin, TB259 (Feb. 1999) pp. 1-14.

Promega Corporation—Wizard® PureFection Plasmid DNA Purification System, Neural. Notes, vol. 4, Issue 2 (1998) p. 14.

Promega Corporation—Wizard® Purification Systems Brochure, BR072 (Jul. 1998) pp. 1-7.

Promega DNA IQ System-Database Protocol, TB 297, revised Jun. 2002.

Promega DNA IQ System-Small Sample Casework Protocol, TB296, revised Jun. 2002.

Promega, Technical Bulletin No. 117 "Wizard Miniprep" (Dec. 1994).

QIAGEN Plasmid Purification Handbook (Jan. 1997) 67 pages.

Quantiblot, Quantiblot Human DNA Quantitation System, PE Applied Biosystems, Feb. 5, 1996, p. 1-5 (http://www.pebio.com/fo/773503/773503.html).

Rassi, Z.E. et al., "Tandem columns and mixed-bed columns in high-performance liquid chromatography of proteins," J. Chrom. (1986) 359:255-264.

Rudi, K. et al., "Rapid, universal method to isolate PCR-ready DNA using magneteic beads," BioTechniques (1997) 22:506-511.

Sambrook et al., Molecular Cloning a Laboratory Manual, 2nd edition, Cold Spring Harbor Laboratory Press (1989) pp. 1.25-1.28.

Sambrook, J. et al., "Extraction and purification of plasmid DNA," Molecular Cloning, a Laboratory Manual, Second Edition, Cold Harbor Laboratory Press (1998) 1.21-1.45.

Sambrook, J. et al., Molecular Cloning a Laboratory Manual, 2nd edition, Cold Spring Harbor Laboratory Press (1989) p. 2.22 and filtration system reference.

Scott, D.L. Jr. et al., "The use of biomagnetic separation to recover DNA suitable for PCR from claviceps species," Lett. Appl. Microbiol: (2000) 31:95-99.

Shiels, G, et al., MagneSil™ C'este Magnifique!, Promega Notes 79 (2001), 3 pages.

Shih et al., "Chemical linkage of nucleic acids to neutral and phosphorylated cellulose powders and isolation of specific sequences by affinity chromatography," Biochem. (1974) 13:3411-3418.

Sigma-Aldrich 1997 Catalog, cover and p. 448.

Smith, D. et al., "Automated purification of plasmid DNA using paramagnetic particles," Jala V.8(3) pp. 50-54 (Jun. 2003).

Sparkes et al., "The validation of a 7-locus multiplex STR test for use in forensic casework," Int. J. Legal Med. (1996) 109:195-204.

Su et al., "Cellulose as a matrix for nucleic acid purification," Anal. Biochem. (1999) 267:415-418.

Taylor, J.I. et al., "Application of magnetite and silica-magnetite composites to the isolation of genomic DNA," J. Chromatography A (2000) 890:159-166.

Tereba et al., "Simultaneous purification and quantitation of DNA from liquid blood and bloodstains," submitted on Mar. 1, 1999 to the International Association of Forensics Sciences (IAFS) Meeting, Aug., 1999.

Tuschl, T. et al., "Small interfering RNAs: a revolutionary tool for the analysis of gene function and gene therapy," A Role for siRNAs in Genetic Therapy, Molecular Interventions (2002) 2(3):158-167.

Vogelstein et al., "Preparative and analytical purification of DNA from Agarose," PNAS (1979) 76(2):615-619.

Waterborg et al., "Efficient large-scale purification of restriction fragments by solute-displacement ion-exchange HPLC," Nucleic Acids Res. (1993) 21(12):2913-2915.

Weber et al., "Effects of lipopolysaccharide on transfection efficiency in eukaryotic cells," Biotechniques (1995) 19(6):930-940.

Weith et al., "Synthesis of cellulose derivatives containing the dihydroxyboryl group and a stufy of their capacity to form specific complexes with sugars and nucleic acid components," Biochem. (1970) 9:4396-4401.

Wheatley, J.B., "Multiple ligand applications in high-performance immunoaffmity chromatography," J. Chromatogr. (1992) 603:273.

White, D., et al., "Automated purification of transfection-grade plasmid DNA using Wizard MagneSil Tfx System," JALA, v. 8(4), pp. 50-53 (2003).

White, D., et al., "Be a "Wizard" at transfection," Promega Notes 83 (2003) pp. 18-20.

White, D., et al., "Cells to Gels: Automated purification of plasmid DNA directly from bacterial culture with normalization," Promega Notes, No. 85 (2003) pp. 28-30.

White, D., et al., MagneSil™ paramagnetic particles: Novel magnetics for DNA purification, Promega Notes, No. 69 (1998) pp. 12-15.

White, D., et al., Wizard® PureFection plasmid DNA purification system: The new standard in isolating transfection grade plasmid DNA, Promega Notes, No. 68 (1998) pp. 2-9.

Wicks et al., "Bacterial lipopolysaccharide copurifies with plasmid DNA: implications for animal models and human gene therapy," Human Gene Therapy (1995) 6:317-323.

Wirth, M.J. et al., "Mixed self-assembled monolayers in chemical separations," Science (1997) 275:44-47.

Wolfe, K.A. et al., "Toward a microchip-based solid-phase extraction method for isolation of nucleic acids," Electrophoresis (2002) 23(5):727-733.

Zhang, Y-P. et al., "A small-scale procedure for extracting nucleic acids from woody plants infected with various phytopathogens for PCR assay," J. Virol. Meth. (1998) 71:45-50.

International Search Report and Written Opinion for Application No. PCT/US2010/047137 dated Dec. 9, 2010 (8 pages).

International Search Report and Written Opinion for Application No. PCT/US2010/047139 dated Jan. 20, 2011.

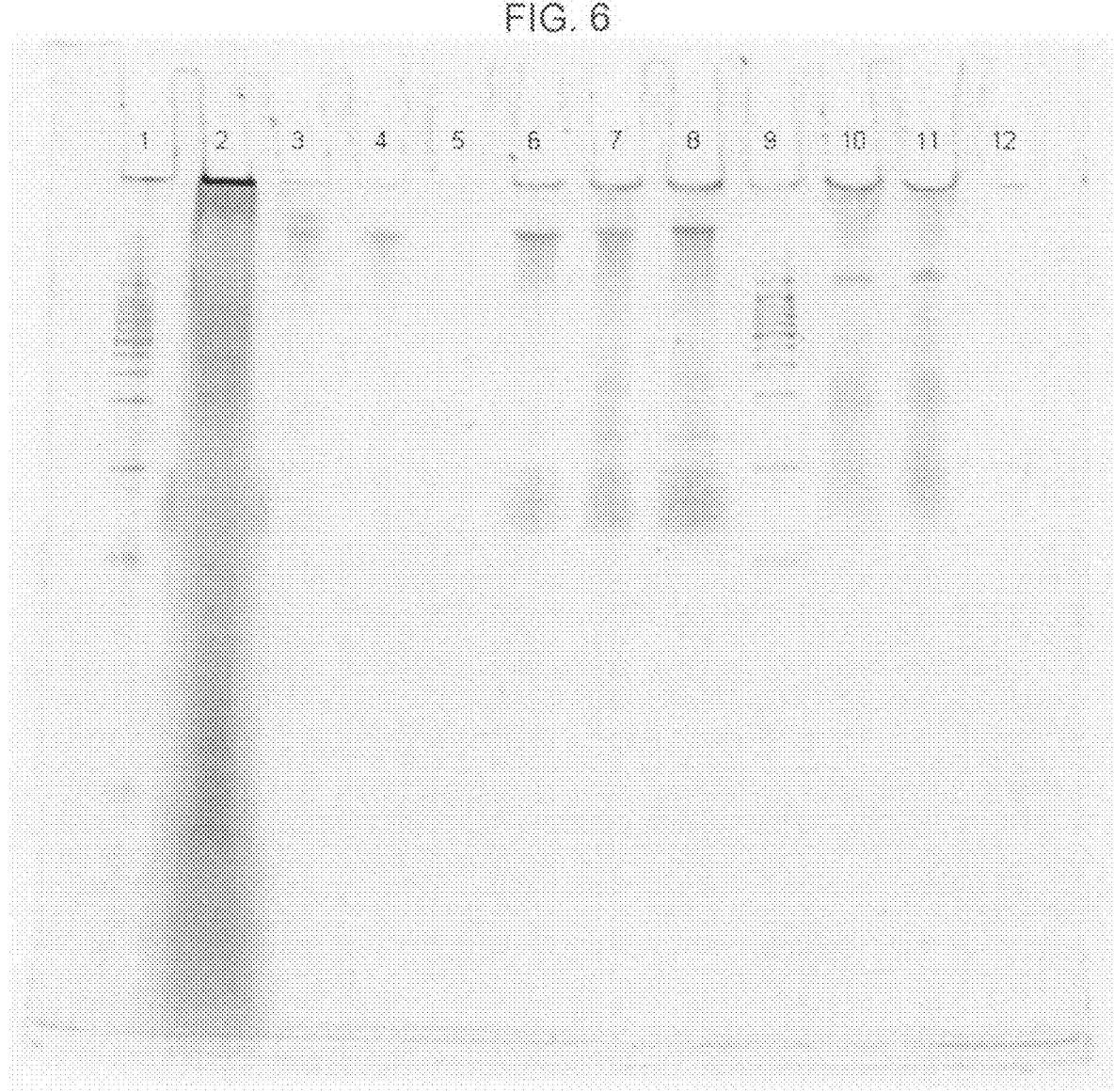

US 8,039,613 B2

METHODS OF PURIFYING A NUCLEIC ACID AND FORMULATION AND KIT FOR USE IN PERFORMING SUCH METHODS

FIELD OF THE INVENTION

This invention relates to methods of purifying one or more nucleic acids, and also to a formulation and kit for use in performing such methods.

BACKGROUND OF THE INVENTION

The purification of nucleic acids plays an important role in scientific procedures. There are a number of known methods of purifying single- and double-stranded DNA contained in biological fluids such as human blood, serum, and cultured cells, as well as plants, animal and human tissues, and other specimens. However, such methods can result in very low yields and do not always work well when trying to extract small amounts of nucleic acids from large samples. Known methods are described in, for example, Nargessi, U.S. Pat. No. 6,855,499 (2005); Tereba et al., U.S. Pat. No. 6,673,631 (2004); McKernan et al., U.S. Pat. No. 6,534,262 (2003); Taylor et al., *J. Chromatography A*, 890:159-166 (2000); Ahn et al., *BioTechniques*, 29:466-468 (2000); Scott Jr. et al., *Lett. Appl. Microbiol.*, 31:95-99 (2000); Lin et al., *BioTechniques*, 29:460-466 (2000); Smith et al., U.S. Pat. No. 6,027,945 (2000); Mrazek et al., *Acta Univ. Palacki. Olomuc., Fac. Med.* 142:23-28 (1999); Hawkins, U.S. Pat. No. 5,898,071 (1999); and Hawkins, U.S. Pat. No. 5,705,628 (1998).

SUMMARY OF THE INVENTION

The present invention represents an improvement over the known methods described in the aforementioned literature.

In one aspect, the invention relates to a method of purifying at least one nucleic acid, such as deoxyribonucleic acid (DNA), ribonucleic acid (RNA), and/or peptide nucleic acid (PNA), which is contained in a medium, such as whole blood, plasma, or tissue cell cultures obtained from humans, plants, or animals. The method includes steps of (a) combining the medium containing the at least one nucleic acid with at least one binding matrix and a formulation in order to cause the at least one nucleic acid to separate from its in vivo cellular environment and bind to at least one binding matrix, (b) separating the binding matrix with at least one nucleic acid bound thereto from substantially the rest of the combined medium and formulation, and (c) eluting the at least one nucleic acid from the binding matrix, thereby obtaining the at least one nucleic acid in a substantially purified form.

A nucleic acid is considered to be in a "substantially purified form" when the nucleic acid has been separated from its in vivo cellular environment and obtained in a form that is useful in one or more scientific procedures, such as the isolation of genetic material, polymerase chain reactions, electrophoresis, sequencing, and cloning, among others.

The formulation used in the foregoing method contains an amount of guanidine thiocyanate and an amount of (i) acetamide, (ii) one or more acetamide derivatives, or (iii) a combination of acetamide and one or more acetamide derivatives. Preferred acetamide derivatives include methylacetamide and dimethylacetamide. Herein, guanidine thiocyanate is sometimes referred to as "GTC," and the combination of guanidine thiocyanate with acetamide and/or one or more acetamide derivatives is sometimes referred to as "GTC-A."

In the above method, the respective amounts of GTC and acetamide and/or acetamide derivative(s) present in the formulation are sufficient to cause the at least one nucleic acid to separate from its in vivo cellular environment and bind to the binding matrix. Preferably, the concentration of GTC in the formulation is from approximately 1.7M to approximately 4.3M, more preferably from approximately 4.0M to approximately 4.3M. Preferably, the concentration of acetamide and/or acetamide derivative(s) in the formulation is from approximately 5.0M to approximately 7.5M, more preferably from approximately 5.0M to approximately 7.1M.

Any of a number of known binding matrices can be used in the foregoing method, depending on the type of nucleic acids sought to be purified. Those skilled in the art will be able to select binding matrices that are compatible with the nucleic acid of interest. Examples of suitable binding matrices include, but are not limited to, paramagnetic cellulose particles, paramagnetic carboxy-cellulose particles, paramagnetic citrus pectin particles, paramagnetic apple pectin particles, paramagnetic zeolite particles, paramagnetic silica particles, cellulose membranes, silica membranes, cellulose acetate columns, nylon membrane columns, PVDF membrane columns, polypropylene columns, HIGH PURE™ spin columns (available from Roche-Diagnostics, item 1 828 665), and clearing columns.

The ratio of formulation to medium used in the above method is preferably from 1:1 to 30:1, more preferably from 1.5:1 to 8:1, by volume. The ratio of binding matrix to medium is preferably from 0.005:1 to 0.5:1, more preferably from 0.2:1 to 0.4:1, by volume. One skilled in the art will be able to select proportions, within or outside of these preferred ranges, depending on the nucleic acid(s) of interest, the concentration of the formulation, and the type of binding matrix employed, among other variables. Therefore, the invention is not limited to these preferred ranges.

Optionally, one or more additional ingredients can be combined with the medium, the binding matrix, and the formulation. For example, one or more enzymes which aid in the degradation and lysis of cellular structure can be used to facilitate the separation of nucleic acids from their mediums. Examples of suitable additional ingredients include, but are not limited to, proteinase K (available from Promega, catalog item V3021), beta-mercaptoethanol (BME), tris(carboxyethyl)phosphine (TCEP), dithiothreitol (DTT) (available from Sigma, catalog item 43815), 1-thioglycerol (1-TG) (available from SIGMA-ALDRICH™, catalog item M2172), digitonin, lysis solutions, CHAPS (3-[(3-cholamidopropyl)dimethylammonio]-1-propanesulfonate; available from SIGMA-ALDRICH™, catalog item C3023), TERGITOL™ type NP-9 (26-(4-nonylphenoxy)-3,6,9,12,15,18,21,24-octaoxahexacosan-1-ol; available from SIGMA-ALDRICH™, catalog item np9), and TRITON™ X-100 (4-(1,1,3,3-tetramethylbutyl)phenyl-polyethylene glycol; available from Thermo Scientific, Waltham, Mass., catalog item BP151). How these additional ingredients are employed is not critical. For example, they can be incorporated in the formulation or they can be added to the medium either before or after the medium is combined with the binding matrix and/or the formulation.

This method can also be used to purify at least two different nucleic acids contained in a single medium. This involves combining a medium containing at least two different nucleic acids with a first binding matrix compatible with a first nucleic acid contained in the medium, a second binding matrix compatible with a second nucleic acid contained in the medium, and a GTC-A formulation as described above. This causes the first and second nucleic acids to separate from their in vivo cellular environments and to bind to the first and second binding matrices, respectively. Each of the first binding matrix with the first nucleic acid bound thereto and the second binding matrix with the second nucleic acid bound thereto then is separated from substantially the rest of the combined medium and formulation. Further, the first nucleic acid is eluted from the first binding matrix, and the second nucleic acid is eluted from the second binding matrix, thereby obtaining each of the first and second nucleic acids in a substantially purified form.

Optionally, a medium containing the second nucleic acid and the formulation can be transferred after the first nucleic acid contained in the medium binds to the first binding matrix. This is followed by a transfer of the remaining medium to the second binding matrix compatible with the binding of the second nucleic acid contained in the medium, before separating each of the first and second nucleic acids from the first and second binding matrices, respectively.

In another aspect, the invention relates to a method as described above, except that the final eluting step is not necessarily required, although such a step is not excluded. Thus, the binding matrix with the nucleic acid bound thereto can be stored and/or transported for later use in scientific procedures, which may or may not involve eluting the nucleic acid from the binding matrix.

In another aspect, the invention relates to a kit for use in purifying nucleic acids and/or binding nucleic acids to a binding matrix. The kit includes a binding matrix and a GTC-A formulation as described above. Preferably, the ratio of binding matrix to formulation in the kit is within the range of from 1:400 to 1:1, by volume. The ratio of binding matrix to formulation can be varied within or outside of this preferred range depending on, among other things, the nucleic acid(s) of interest and the type of binding matrix employed.

BRIEF DESCRIPTION OF THE FIGURES

FIG. 6 is a photograph showing the results of an electrophoresis analysis performed in accordance with Example 8, described below.

DETAILED DESCRIPTION OF THE PREFERRED EMBODIMENTS

Figure 1:
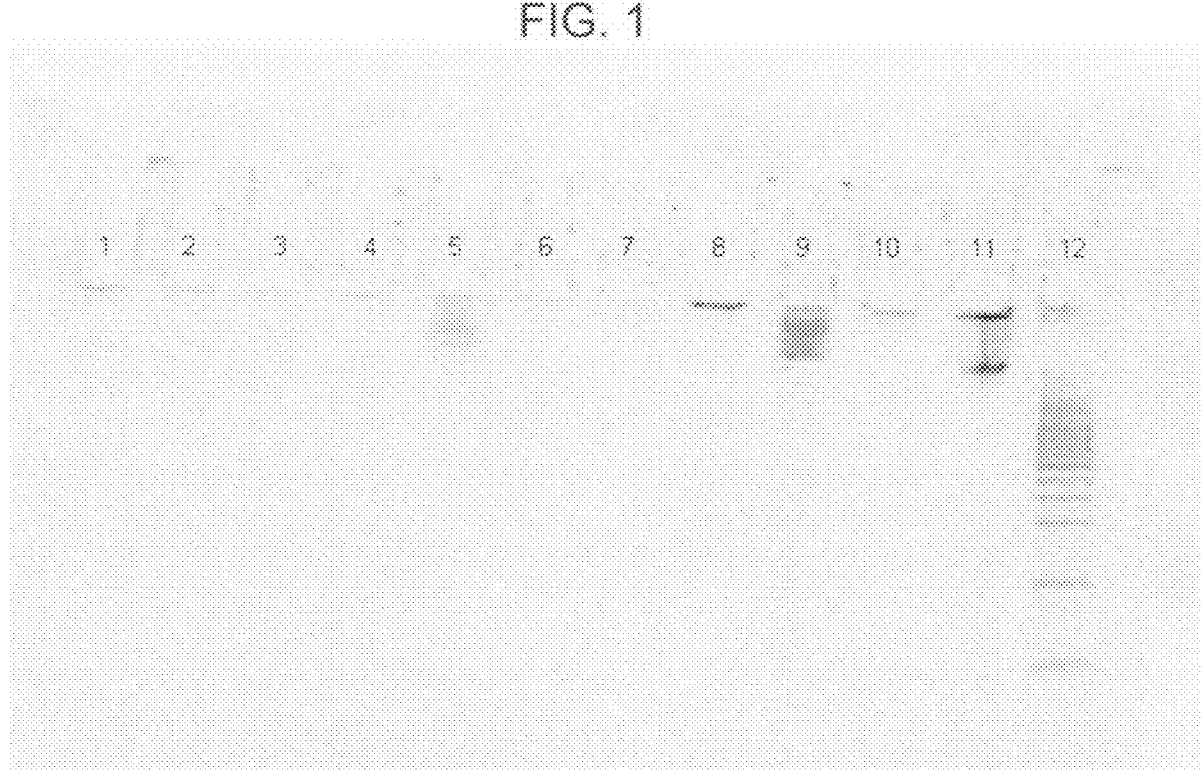
FIG. 1 is a photograph showing the results of an electrophoresis analysis performed in accordance with Example 2, described below.

The following are non-limiting examples of preferred implementations of the present invention. Throughout, all volumes, pH levels, and concentrations are at room temperature unless stated otherwise.

Nucleic Acids

The nucleic acids capable of being purified using the present invention include, but are not limited to DNA (single-stranded, double-stranded, covalently closed, and relaxed circular forms), RNA (single-stranded and double-stranded), PNA, and hybrids of the foregoing.

Nucleic-Acid-Containing Mediums

As used herein, the term "medium" encompasses any biological material, either naturally occurring or scientifically engineered, that contains at least one nucleic acid in addition to other non-nucleic acid material, such as biomolecules (e.g., proteins, polysaccharides, lipids, low molecular weight enzyme inhibitors, oligonucleotides, primers, templates), polyacrylamide, trace metals, organic solvents, etc. Examples of naturally-occurring mediums include, but are not limited to, whole blood, plasma, and other body fluids, as well as tissue cell cultures obtained from humans, plants, or animals. Examples of scientifically-engineered mediums include, but are not limited to, lysates, nucleic acid samples eluted from agarose and/or polyacrylamide gels, solutions containing multiple species of DNA molecules resulting either from a polymerase chain reaction (PCR) amplification or from DNA size selection procedures, and solutions resulting from post-sequencing reactions.

Binding Matrix

Advantageously, one or more binding matrices can be used in the present invention. As used, herein, the term "binding matrix" encompasses any form capable of binding a nucleic acid. Those skilled in the art will be able to select an appropriate binding matrix for the nucleic acid(s) of interest.

Examples of suitable binding matrices include MAGA-ZORB™ paramagnetic particles (available from Promega, Madison, Wis., catalog item MB1001), GENFIND™ particles (available from BECKMAN-COULTER™, Fullerton, Calif.), MAGNESIL™ Blue paramagnetic silica particles (available from Promega, catalog item A2201), zeolite particles (see Bitner et al., U.S. Published Patent Appln. No. 2007/0172855, the entirety of which is incorporated by reference herein), and paramagnetic apple or citrus pectin particles (see Example 1 below). Other suitable binding matrices include, without limitation, paramagnetic silica particles, cellulose membranes, silica membranes, or columns such as cellulose acetate columns, nylon membrane columns, PVDF membrane columns, polypropylene columns, pure spin columns, and clearing columns for use in DNA IQ™ spin baskets (available from Promega, catalog item V1221). More specifically, suitable columns include DNA-IQ™ columns, SV columns, Corning spin columns (available from Corning of Corning, N.Y., catalog item 8160), nylon membrane Corning spin columns (available from Corning, catalog item 8169), PVDF membrane in a polypropylene spin columns (available from Millipore Ultrafree-MC of Beverly, Mass., catalog item VFC30GVNB), polypropylene membrane (available from Corning, catalog item AN0604700) in a DNA-IQ™ column, HIGH PURE™ Spin Filter tubes (available from Roche of Indianapolis, Ind., catalog item 1828665), and clearing columns (available from Promega, catalog item Z568A). Schleicher & Schuell cellulose cards (available from Keene of NH, catalog item GB003) also provide a useful binding matrix, particularly when storing and/or transporting nucleic acids for later use in downstream procedures.

The ratio of binding matrix to medium is preferably from 0.005:1 to 0.5:1, more preferably from 0.2:1 to 0.4:1, by volume. One skilled in the art will be able to select optimal proportions, within or outside of these preferred ranges, depending on the nucleic acid(s) of interest and the type of binding matrix, among other factors.

GTC-A Formulation

The GTC-A formulation acts as a lysis and/or binding solution that separates the nucleic acid of interest from its in vivo cellular environment and, if a binding matrix is present, facilitates the binding of the nucleic acid to the binding matrix. As mentioned above, the formulation contains an amount of GTC and an amount of acetamide and/or one or more acetamide derivatives. The GTC and acetamide and/or one or more acetamide derivatives may be added together, or sequentially to the sample medium. As an example of sequential addition, the GTC may be added to the sample medium in a first solution, for example, to lyse cells, and the acetamide and/or one or more acetamide derivatives may be added in a second solution, for example, as a binding solution to promote binding of the DNA or RNA to the binding matrix.

As demonstrated by the examples below, other salts or salt and amide combinations, such as guanidine hydrochloride (available from Promega, catalog item H5381), guanidine hydrochloride and acetamide, GTC alone, or acetamide alone, are relatively ineffective in the purification of nucleic acids. Surprisingly, even though neither GTC alone nor acetamide alone is effective in purifying nucleic acids, the combination of GTC and acetamide and/or acetamide derivative(s) is highly effective.

The respective amounts of GTC and acetamide and/or acetamide derivative(s) present in the GTC-A formulation can be adjusted to various concentrations. The concentration of GTC in the formulation is preferably from approximately 1.7M to approximately 4.3M, more preferably from approximately 4.0M to approximately 4.3M. The concentration of acetamide and/or acetamide derivative(s) in the formulation is preferably from approximately 5.0M to approximately 7.5M, more preferably from approximately 5.0M to approximately 7.1M.

The proportion of formulation to medium depends on a number of variables, including, without limitation, the concentration of the formulation, the nucleic acid(s) of interest, whether a binding matrix is used, and, if so, what type. A preferred range of ratios of formulation to medium is from 1:1 to 30:1, by volume. A more preferred range is from 1.5:1 to 8:1, by volume.

GTC can be purchased from Promega, catalog item V2791. Acetamide can be purchased from SIGMA-ALDRICH™, catalog item A0500-500G. As mentioned, GTC can also be used with derivatives of acetamide. Preferred acetamide derivatives include N-methylacetamide (available from ACROS of Fair Lawn, N.J., catalog item 126141000) and N,N-dimethylacetamide (available from SIGMA-ALDRICH™, catalog item D5511). Sometimes, such as when purifying RNA from HEK293 tissue cells, the use of GTC and N,N-dimethylacetamide is preferred over the use of GTC and acetamide or GTC and N-methylacetamide.

Optionally, the GTC-A formulation can further contain one or more additional ingredients such as, for example, proteinase K, beta-mercaptoethanol, tris(carboxyethyl)phosphine, dithiothreitol, 1-TG, digitonin, lysis solutions, CHAPS, TERGITOL™ type NP-9, and TRITON™ X-100.

In addition to being used as a lysis and/or binding solution, the GTC-A formulation can also be used as a wash solution for removing impurities, as described in the methods below.

Kits

The GTC-A formulation can be combined with one or more binding matrices in a kit that can be used in the purification of nucleic acids. Preferably, the ratio of binding matrix to formulation in the kit is within the range of from 1:400 to 1:1, by volume. The ratio of binding matrix to formulation can be varied within or outside of this preferred range, depending on the specific contents of the kit and the application for which the kit is intended. The kit may comprise GTC in a first container, and acetamide and/or one or more acetamide derivatives in a second container, combined with one or more binding matrices in a kit that can be used in the purification of nucleic acids. Alternatively, the GTC and acetamide and/or one or more acetamide derivatives may be combined in a single container. The one or more binding matrices may be combined within one of the above containers, or provided as a separate item in a kit that can be used in the purification of nucleic acids.

Advantageously, the kit can include more than one type of binding matrix, each compatible with a different type of nucleic acid. In that case, the kit can be used in the selective purification of different types of nucleic acids.

First Method

In one preferred implementation, the invention relates to a method of purifying at least one nucleic acid contained in a medium. The medium containing the at least one nucleic acid is combined with at least one binding matrix and a GTC-A formulation in order to cause the at least one nucleic acid to separate from its in vivo cellular environment and bind to at least one binding matrix. The medium, binding matrices, and GTC-A formulation can be combined in any order or simultaneously. The binding matrices with at least one nucleic acid bound thereto then is separated from substantially the rest of the combined medium and formulation, for example, by using a magnetic rack, by centrifuging, or by filtration. Optionally, at this point, bound binding matrix and the nucleic acid combinations can be washed using any suitable wash solution, including the GTC-A formulation, in order to remove any impurities. Thereafter, the at least one nucleic acid is eluted from the binding matrix, thereby obtaining the at least one nucleic acid in a substantially purified form. This elution step can immediately follow the aforementioned steps, or it can be performed at a later time. By choosing to elute the nucleic acid from the binding matrix at a later time, the nucleic acids can be stored for downstream activities.

In more detail, the elution step uses an elution buffer to separate the nucleic acid from the binding matrix, after which the substantially purified nucleic acid is contained in the elution buffer. Suitable elution buffers include, but are not limited to, nuclease-free water or aqueous solutions such as, for example, TRIS™-HCl, Tris-acetate, sucrose, and formamide solutions. A preferred elution buffer is a TRIS™ buffer with ethylenediaminetetraacetic acid (EDTA). More preferably, the elution buffer is about 10 mM TRIS™ (pH 8.0) and about 1 mM EDTA HEPES™ (pH 7.5). Elution of the nucleic acid from the binding matrix occurs quickly (e.g., in thirty seconds or less) when a suitable low ionic strength elution buffer is used.

Following purification, the nucleic acids can be used in any of a number of known scientific procedures, including, without limitation, the isolation of genetic material, polymerase chain reactions, electrophoresis, sequencing, cloning, and the like.

This method can also be used to purify at least two different nucleic acids contained in a single medium. This involves combining a medium containing at least two different nucleic acids with a first binding matrix compatible with binding a first nucleic acid contained in the medium, and a second binding matrix compatible with binding a second nucleic acid contained in the medium, and a GTC-A formulation as described above. This causes the first and second nucleic acids to separate from their in vivo cellular environments and to bind to the first and second binding matrices, respectively. Each of the first binding matrix with the first nucleic acid bound thereto and the second binding matrix with the second nucleic acid bound thereto then is separated from substantially the rest of the combined medium and formulation. Then, the first nucleic acid is eluted from the first binding matrix, and the second nucleic acid is eluted from the second binding matrix, thereby obtaining each of the first and second nucleic acids in a substantially purified form. Alternatively, this method involves combining a medium containing at least two different nucleic acids with a first binding matrix compatible with binding a first nucleic acid contained in the medium (e.g. DNA-IQ™ particles which are compatible with binding DNA), followed by a transfer of the remaining solution depleted of the first nucleic acid (e.g., the RNA remaining after DNA binding to DNA-IQ™ particles) to a second binding matrix (e.g., paramagnetic zeolite particles) compatible with binding of the remaining nucleic acids, thereby separately obtaining each of the first and second nucleic acids in a substantially purified form.

Second Method

In another implementation, the invention relates to a method as described above, except that this method does not necessarily require eluting the nucleic acid from the binding matrix. Rather, the binding matrix with the nucleic acid(s) bound thereto can be stored and/or transported for later use in scientific procedures, which may or may not involve eluting the nucleic acid(s) from the binding matrix.

This method is particularly useful when using the Schleicher & Schuell cellulose card as the binding matrix. When there is a need for purified nucleic acids, a hole can be punched from the cellulose card and the nucleic acid bound thereto can be eluted for use in a scientific procedure.

Example 1

In this example, paramagnetic apple or citrus pectin particles suitable for use in certain embodiments of the present invention as a binding matrix were prepared as follows:
1. In a beaker, mix 0.5 gm of $Fe_3O_4$ particles (magnetite, available from SIGMA-ALDRICH™ of St. Louis, Mo., catalog item 31,006-9) with 1.0 gm of apple pectin particles (available from SIGMA-ALDRICH™, catalog item P8471) or citrus pectin particles (available from SIGMA-ALDRICH™, catalog item P9135) in 8 ml of water.
2. Adjust the pH of the mixture, first by adding 3.0 ml of 56% KOH. After mixing for 5 minutes at about 21° C., lower the pH by adding 3.3 ml of 3.0M HCl, with periodic testing of the mixture's pH using pH paper. The resulting pH should be about 3. Next, add 3.5 ml of 1.32M KOAc having a pH of 4.8 so that the resulting pH of the mixture is between 4 and 5.
3. Allow the mixture to sit overnight at about 21° C. Some large (e.g., 1-2 $cm^3$) particles will form and settle to the bottom of the beaker. Pour off the rest of the mixture into a tube, and label the beaker containing the large particles as "large."
4. Place the tube containing the rest of the mixture on a magnetic rack and magnetize the mixture. After 2 minutes, pour off the portion of the mixture that has not been attracted to the side wall of the tube into another tube. Label the tube containing the particles that were attracted to the side wall as "main." There should be approximately 3 ml of "main" particles, ranging anywhere from about 0.6 µm to about 80 µm in size.
5. Place the tube containing the rest of the mixture back on the magnetic rack and magnetize the mixture. After 10 minutes, pour off and discard the portion of the mixture that has not been attracted to the side wall of the tube. Label the tube containing the particles that were attracted to the side wall as "first cut." There should be approximately 1.5 ml of "first cut" particles.
6. Wash the "large," "main," and "first cut" particles three times with nanopure water to remove any residual KOAc and/or residual pectin particles. For each wash, add 10 ml of the nanopure water to the set of particles, allow the particles to settle, and then pour off the nanopure water.

Any of the three sets of paramagnetic pectin particles—"large," "main," and "first cut"—can be used as a binding matrix; however, in the examples that follow, only the "main" particles are used.

Example 2

In this example, nine different lysis-binding formulations were used, some more successfully than others, in an attempt to purify DNA from human whole blood samples. The following procedure was used:
1. Prepare nine samples, 1-9, by adding 50 µl of MAGAZORB™ paramagnetic particles, followed by 200 µl of human whole blood (available from Bioreclamation, Inc., Hicksville, N.Y., catalog item HMPLEDTA3), to each of nine 1.5 ml plastic tubes.
2. Add 800 µl of one of the following nine formulations to a different one of samples 1-9 as follows: (a) to sample 1, add 5.0M acetamide; (b) to sample 2, add 2.6M guanidine hydrochloride (GHCl); (c) to sample 3, add a mixture of 2.6M GHCl and 5.0M acetamide; (d) to sample 4, add 2.6M GTC; (e) to sample 5, add a mixture of 2.6M GTC and 5.0M acetamide; (f) to sample 6, add a mixture of 4.3M GHCl and 5.0M acetamide; (g) to sample 7, add 6.5M GHCl; (h) to sample 8, add 9.0M acetamide; and (i) to sample 9, add a mixture of 4.3M GTC and 5.0M acetamide. Mix each sample thoroughly by repeated pipetting.
3. Allow each sample to sit for 10 minutes at about 21° C., and then place each sample on a magnetic rack in order to separate the MAGAZORB™ paramagnetic particles from the rest of the sample. Remove and discard the supernatants, leaving only the MAGAZORB™ paramagnetic particles.
4. Remove each of samples 1-9 from the magnetic rack and wash the MAGAZORB™ paramagnetic particles with 800 µl of RNA Wash Solution (available from Promega, catalog item Z3091), mixing the particles into the solution by pipetting. Place each sample back on the magnetic rack in order to separate the MAGAZORB™ paramagnetic particles from the rest of the sample. Again, remove and discard the supernatants, leaving only the MAGAZORB™ paramagnetic particles.
5. Repeat step 4 in order to wash the MAGAZORB™ paramagnetic particles a second time.
6. Allow samples 1-9 to air dry on the magnetic rack for 20 minutes at a temperature of about 21° C.
7. Remove the samples from the magnetic rack and elute the DNA from the MAGAZORB™ paramagnetic particles by adding 200 µl of nuclease-free water at a temperature of about 56° C. to each sample. Allow the samples to elute for 20 minutes, occasionally vortexing each sample to release the DNA from the MAGAZORB™ paramagnetic particles into the nuclease-free water, and then place the samples back on the magnetic rack.
8. Using blue/orange 6× loading dye (available from Promega, catalog item G190), load 10 µl of the DNA-containing, nuclease-free water from each of samples 1-9 into a respective one of nine agarose gel electrophoresis lanes containing a 15% TBE-urea gel (available from INVITROGEN™, Carlsbad, Calif., catalog item EC68852BOX). To a tenth lane, add nothing. To an eleventh lane, add 10 µl of genomic DNA standard (available from Promega, catalog item G3041) to serve as a control. To a twelfth lane, add 10 µl of 100 bp DNA ladder of standard molecular weight (available from Promega, catalog item G2101) to serve as a scale.
9. Perform electrophoresis using bromphenol blue dye at 120 volts for about 3 hours or until the bromphenol blue dye reaches the bottom slit of the gel. Stain each lane for 15 minutes with SYBR™ Gold (available from INVITROGENT™, catalog item S11494), and digitally image all of the lanes using an ALPHA INNOTECH FLUOROCHEM™ Imaging System, and, in particular, the Amersham TYPHOON™ platform with settings of: 1. ex488/em526. 2. PMT 450.

FIG. 1 shows the results of the electrophoresis analysis of the samples prepared according to Example 2. In FIG. 1, the lanes are numbered 1-12, from left to right. Lanes 1-9 show the results for samples 1-9, respectively; lane 10 contains no sample; lane 11 shows the genomic DNA standard; and lane 12 shows the 100 bp DNA ladder of standard molecular weight.

As demonstrated in FIG. 1, in the case of human whole blood, the use of acetamide alone (lanes 1 and 8), GHCl alone (lanes 2 and 7), GTC alone (lane 4), or the combination of acetamide and GHCl (lanes 3 and 6) did not result in substantial DNA purification. Surprisingly, even though neither GTC alone nor acetamide alone was effective, using a combination of GTC and acetamide (lanes 5 and 9) resulted in substantial DNA purification.

Example 3

In this example, DNA from human whole blood samples was purified using a GTC-A formulation together with each of four different binding matrices using the following procedure:
1. Prepare eight samples, 1-8, by adding 800 µl of "$L_1$," which consists of 2.7M GTC and 6.8M acetamide, to each of eight 1.5 ml plastic tubes.
2. To each sample, add 20 µl of 20 mg/ml proteinase K and mix the sample by pipetting.
3. To each sample, add 100 µl of human whole blood and mix six times by pipetting.
4. Incubate each sample for five minutes at a temperature of about 56° C., mix each sample by pipetting, and then incubate each sample for an additional five minutes at about 56° C.
5. Add one of the four aforementioned binding matrices to each of samples 1-8 as follows: (a) to each of samples 1 and 2, add 40 µl (1.9 mg) of MAGAZORB™ paramagnetic particles; (b) to each of samples 3 and 4, add 3 µl of paramagnetic carboxy-cellulose GENFIND™ particles; (c) to each of samples 5 and 6, add 40 µl (2.8 mg) of "main" paramagnetic citrus pectin particles (from Example 1); and (d) to each of samples 7 and 8, add 40 µl (4.2 mg) of MAGNESIL™ Blue paramagnetic silica particles. Mix each sample by pipetting and let the samples stand for 10 minutes at a temperature of about 21° C.
6. Magnetize the samples by placing them on a magnetic rack. Remove the excess fluid, so that only the magnetized particles remain for each sample.
7. Remove the samples from the magnetic rack and wash each sample by adding 500 µl of $L_1$ and mixing by pipetting. Next, magnetize the samples by placing them back on the magnetic rack. Remove the excess fluid, so that only the magnetized particles remain for each sample.
8. Repeat the wash a second and third time using 500 µl of $L_1$ by following the procedure of step 7.
9. Wash each sample one additional time using 500 µl of Alcohol Wash, Blood (available from Promega, catalog item MD1411) by following the above wash procedure of step 7, except substituting the Alcohol Wash, Blood for $L_1$.
10. Allow the samples to air dry on the magnetic rack for 10 minutes at a temperature of about 21° C.
11. Remove the samples from the magnetic rack and elute the DNA from the particles by adding 200 µl of 10 mM TRIS™ HCl (pH 8.0) to each sample. Allow the samples to elute for 10 minutes, occasionally vortexing each sample to release the DNA from the particles into the TRIS™ HCl, and then place the samples on a magnetic rack.
12. Using blue/orange 6× loading dye, load 8 µl of the DNA-containing TRIS™ HCl from each of samples 1-8 into a respective one of eight agarose gel electrophoresis lanes containing a 15% TBE-urea gel.
13. Perform electrophoresis using bromphenol blue dye at 120 volts for about 3 hours or until the bromphenol blue dye reaches the bottom slit of the gel. Stain each lane for 15 minutes with SYBR™ Gold, and digitally image all of the lanes using an ALPHA INNOTECH FLUOROCHEM™ Imaging System, and, in particular, the Amersham TYPHOON™ platform with settings of: 1. ex488/em526. 2. PMT 450.

Figure 2:
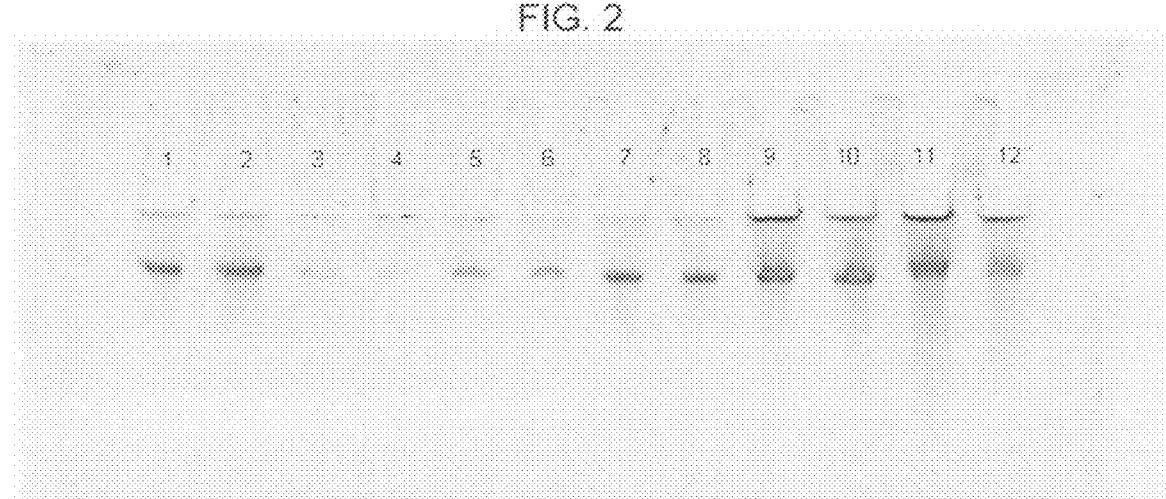
FIG. 2 is a photograph showing the results of an electrophoresis analysis performed in accordance with Examples 3 and 4, described below.

FIG. 2 shows the results of the electrophoresis analysis of the samples prepared according to Example 3. In FIG. 2, the lanes are numbered 1-12, from left to right. Lanes 1-8 show the results for samples 1-8, respectively. (Lanes 9-12 relate to Example 4, which is discussed below.)

As shown in FIG. 2, in the case of human whole blood, all of the samples prepared in accordance with Example 3 achieved substantial purification of genomic DNA. The smaller amount of DNA obtained with the paramagnetic carboxy-cellulose GENFIND™ particles (lanes 3 and 4) is believed to be attributable to the small amount (3 µl) of particles used per sample.

Example 4

In this example, DNA from human whole blood samples was released using a GTC-A formulation together with one of two different binding matrices. The following procedure was used:

1. Prepare four samples, 1-4, by adding 800 μl of "$D_X$," which consists of 4.0M GTC, 5.0M acetamide, 20% (volume/volume) 1-TG, 0.64% (weight/volume) CHAPS, 0.64% (volume/volume) TERGITOL™ type NP-9, and 0.16% (volume/volume) TRITON™ X-100, to each of four 1.5 ml plastic tubes.
2. To each sample, add 20 μl of 20 mg/ml proteinase K and mix the sample by pipetting.
3. To each sample, add 500 μl of human whole blood and mix ten times by pipetting.
4. Incubate each sample for 10 minutes at about 21° C., mix each sample by pipetting, and then incubate each sample for an additional 10 minutes at about 21° C.
5. Add one of the following binding matrices to samples 1-4 as follows: (a) to each of samples 1 and 2, add 100 μl (4.8 mg) of MAGAZORB™ paramagnetic particles; and (b) to each of samples 3 and 4, add 100 μl (7 mg) of "main" paramagnetic citrus pectin particles (from Example 1). Mix each sample by pipetting and allow the samples to sit for 10 minutes at about 21° C.
6. Magnetize the samples by placing them on a magnetic rack. Remove the excess fluid, so that only the magnetized particles remain for each sample.
7. Remove the samples from the magnetic rack and wash each sample by adding 500 μl of $D_X$ and mixing by pipetting. Next, magnetize the samples by placing them back on the magnetic rack. Remove the excess fluid, so that only the magnetized particles remain for each sample.
8. For each sample, repeat the wash procedure of step 7 eight more times using 500 μl of $D_X$ each time.
9. Wash each sample twice with 500 μl of Alcohol Wash, Blood using the wash procedure of step 7, except substituting the Alcohol Wash, Blood for $D_X$.
10. Allow the samples to air dry on the magnetic rack for 20 minutes at about 21° C.
11. Remove the samples from the magnetic rack and elute the DNA from the particles by adding 200 μl of 10 mM TRIS™ HCl (pH 8.0) to each sample. Allow the samples to elute for 10 minutes, occasionally vortexing the samples to release the DNA from the particles into the TRIS™ HCl, and place the samples on a magnetic rack.
12. Using blue/orange 6× loading dye, load 8 μl of the DNA-containing TRIS™ HCl from each of samples 1-4 into a respective one of four agarose gel electrophoresis lanes containing a 15% TBE-urea gel.
13. Perform electrophoresis using bromphenol blue dye at 120 volts for about 3 hours or until the bromphenol blue dye reaches the bottom slit of the gel. Stain each lane for 15 minutes with SYBR™ Gold, and digitally image all of the lanes using an ALPHA INNOTECH FLUORO-CHEM™ Imaging System, and, in particular, the Amersham TYPHOON™ platform with settings of: 1. ex488/em526. 2. PMT 450.

Lanes 9-12 of FIG. 2 show the results of the electrophoresis analysis of samples 1-4, respectively. (Lanes 1-8 of FIG. 2 relate to Example 3, discussed above.)

As shown in FIG. 2, in the case of human whole blood, all of the samples prepared in accordance with Example 4 achieved substantial DNA purification. Purification using the MAGAZORB™ paramagnetic particles averaged 4.5 μg of DNA (lanes 9 and 10) and purification using the "main" paramagnetic citrus pectin particles averaged 4.9 μg of DNA (lanes 11 and 12).

Example 5

In this example, RNA from human blood plasma samples was purified using different GTC-A formulations containing selected inhibitors of RNase activity. The following procedure was used:

1. In this example, twenty-three samples, 1-23, are prepared in twenty-three 1.5 ml plastic tubes.
2. Prepare samples 3-12 and 16-22 by adding, to each of seventeen of the tubes, 800 μl of a formulation consisting of 4.3M GTC, 6.0M acetamide, 0.8% CHAPS (weight/volume), 0.8% TERGITOL™ np-9 (volume/volume), 0.2% TRITON™ X-100 (volume/volume), and the indicated one of the following inhibitors to the final concentration indicated: (a) for sample 3, 0.008% BME (volume/volume); (b) for sample 4, 0.016% BME (volume/volume); (c) for sample 5, 0.032% BME (volume/volume); (d) for sample 6, 0.064% BME (volume/volume); (e) for sample 7, 12.5 mg/ml TCEP; (f) for sample 8, 25 mg/ml TCEP; (g) for sample 9, 50 mg/ml TCEP; (h) for sample 10, 100 mg/ml TCEP; (i) for sample 11, 125 mM DTT; (j) for sample 12, 200 mM DTT; (k) for sample 16, 12.5% 1-TG (volume/volume); (l) for sample 17, 20% 1-TG (volume/volume); (m) for sample 18, 33% 1-TG (volume/volume); (n) for sample 19, 330 mM DTT; (o) for sample 20, a mixture of 12.5% 1-TG (volume/volume) and 0.016% BME (volume/volume); (p) for sample 21, a mixture of 20% 1-TG (volume/volume) and 0.032% BME (volume/volume); and (q) for sample 22, a mixture of 12.5% 1-TG (volume/volume) and 125 mM DTT.
3. To each of samples 3-12 and 16-22, add 1.0 μl of luciferase control RNA (available from Promega, catalog item L4561) and mix the sample by pipetting.
4. To each of samples 3-12 and 16-22, add 200 μl of human plasma (available from Bioreclamation, Inc., Hicksville, N.Y., catalog item HMPLEDTA3) and mix the sample by pipetting.
5. Meanwhile, prepare samples 1, 2, 13-15, and 23 by adding, to the other six tubes, the following: (a) for sample 1, 1 μl luciferase control RNA and 200 μl of human plasma; (b) for sample 13, 1 μl luciferase control RNA; (c) for sample 14, 1 μl luciferase control RNA at a temperature of about −20° C.; (d) for sample 23, 200 μl of human plasma; and (e) for each of samples 2 and 15, nothing.
6. Allow each of samples 1-23 to sit for five minutes at about 21° C. Then, add 2 μl (1 mg) of MAGAZORB™ paramagnetic particles to each sample and then mix each sample by pipetting.
7. Allow the samples to sit for three minutes at about 21° C., and then place the samples on a magnetic rack for two minutes. After the two minutes, remove the supernatants from the samples, leaving only the particles.
8. To each of samples 1-23, add 8 μl of blue/orange loading dye (available from Promega, catalog item G1881) and resuspend the particles by mixing them by pipetting.
9. Repeat step 8 five more times for each sample.
10. Using blue/orange 6× loading dye, load 8 μl of each of samples 1-23 into a respective one of twenty-three agarose gel electrophoresis lanes containing a 15% TBE-urea gel.

11. Perform electrophoresis using bromphenol blue dye at 120 volts for about 3 hours or until the bromphenol blue dye reaches the bottom slit of the gel. Stain each lane for 15 minutes with SYBR™ Gold, and digitally image all of the lanes using an ALPHA INNOTECH FLUORO-CHEM™ Imaging System, and, in particular, the Amersham TYPHOON™ platform with settings of: 1. ex488/em526. 2. PMT 450.

Figure 3A:
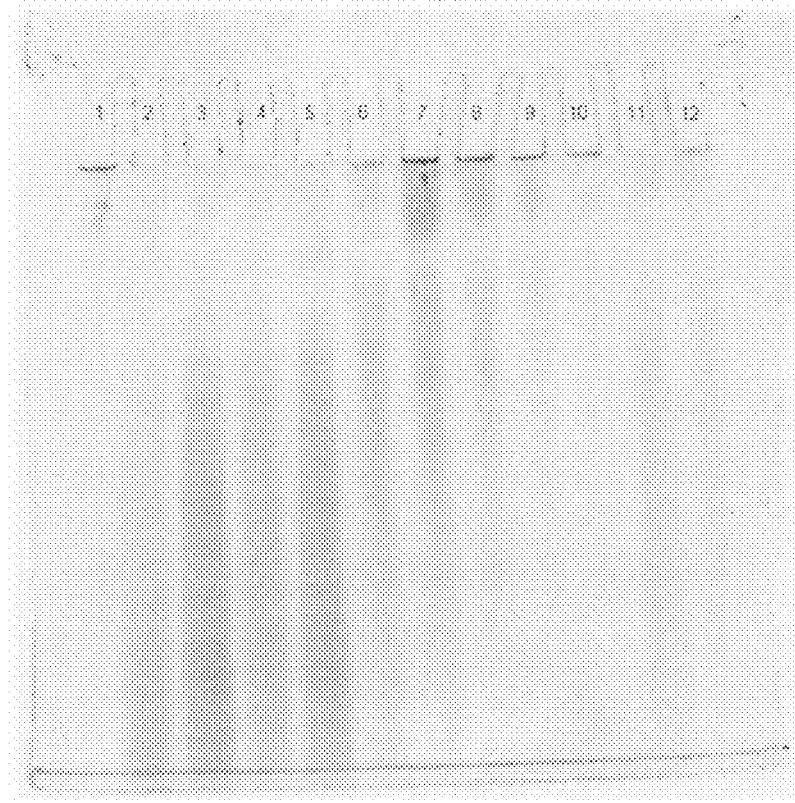
FIGS. 3A and 3B are photographs showing the results of an electrophoresis analysis performed in accordance with Example 5, described below.
Figure 3B:
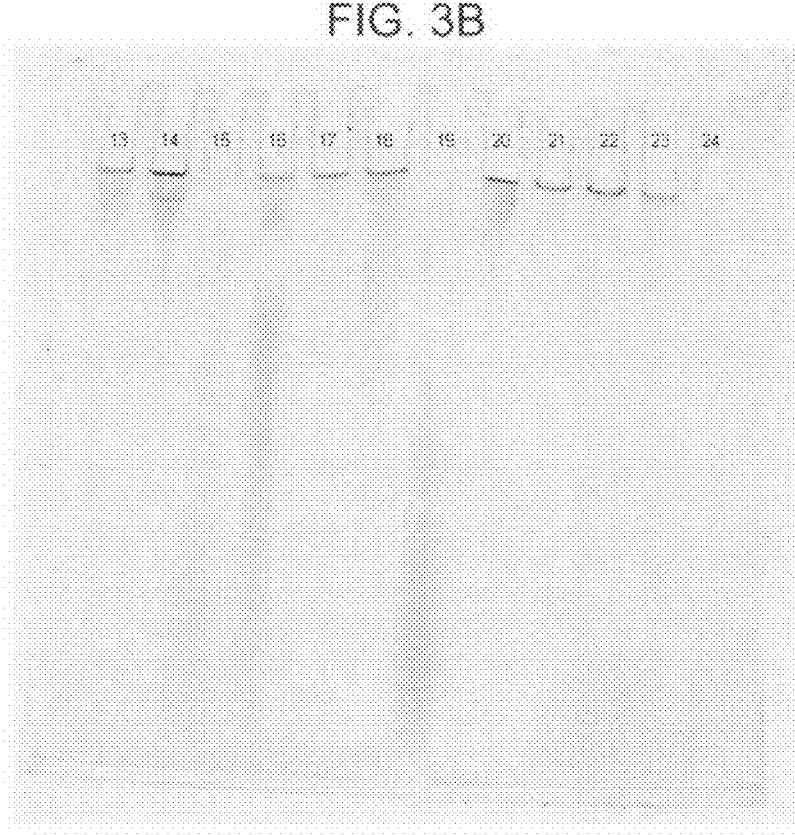

FIGS. 3A and 3B show the results of the electrophoresis analysis of the twenty-three samples prepared according to Example 5. In FIG. 3A, the lanes are numbered 1-12, from left to right. In FIG. 3B, the lanes are numbered 13-24, from left to right. Lanes 1-23 show the results for samples 1-23, respectively. Lane 24 is empty.

As shown in FIGS. 3A and 3B, the GTC-A formulations were effective in the purification of RNA notwithstanding the presence of certain inhibitors. Moreover, the use of certain inhibitors in addition to GTC-A enables the selective purification of RNA, while reducing the degradation of the RNA from RNase during the lysis process. In particular, GTC-A formulations containing BME alone (lanes 3-6) were effective in the purification of larger-sized RNA. Acting as an inhibitor of RNase, the combination of GTC-A and increasing BME concentrations reduced the degradation of the RNA. The GTC-A formulations containing TCEP (lanes 7-10) also inhibited RNA degradation and resulted in less RNA being bound to the MagaZorb® paramagnetic particles than that bound using the GTC-A formulations containing BME. However, the RNA bound to the MAGAZORB™ paramagnetic particles using the GTC-A formulations containing TCEP had a higher average molecular weight than that of the RNA bound using the GTC-A formulations containing BME. 1-TG added to the GTC-A formulation (lanes 16-18 and 20) also resulted in the purification of larger-sized RNA than that obtained using the GTC-A formulations containing BME. 33% 1-TG (lane 18) demonstrated greater inhibition of RNase than 12.5% 1-TG (lane 16). The GTC-A formulations containing BME alone, TCEP alone, and 1-TG alone all demonstrated effective inhibition of RNase. Similarly, the inclusion of both 1-TG and BME in the GTC-A formulation (lane 8) also demonstrated effective RNase inhibition.

Luciferase control RNA added into human blood plasma (lanes 13 and 14) was bound to the MAGAZORB™ paramagnetic particles using the GTC-A formulation. In contrast, the absence of added human plasma (lane 1) demonstrated that the luciferase RNA was not visibly degraded. However, the addition of human plasma (lane 23) resulted in RNA degradation.

Example 6

In this example, DNA as small as about 25 bp in size was purified from human whole blood samples using a GTC-A formulation. The following procedure was used:

1. Prepare twelve samples, 1-12, by adding 200 µl of human whole blood and 800 µl of "$D_1$," the latter of which is made by adding 0.7 gm of CHAPS, 400 µl of TERGITOL™ type NP-9, and 400 µl of TRITON™ X-100 to a 10 ml mixture of 4.3M GTC/5.9M acetamide, to each of twelve 1.5 ml plastic tubes.
2. To each of samples 1-10, add 10 µl of 100 bp DNA ladder.
3. Mix each of samples 1-12 thoroughly by repeated pipetting.
4. To each of samples 1-12, add 30 µl of MAGAZORB™ paramagnetic particles and again mix each sample by pipetting.
5. Incubate each sample for 20 minutes at about 21° C.
6. Into each of samples 1-12, insert a magnetic bar contained within a plastic sleeve, in order to collect the MAGAZORB™ paramagnetic particles.
7. Remove the sleeve/magnetic bar with the collected MAGAZORB™ paramagnetic particles.
8. Place the sleeve/magnetic bar and the collected sample 1-12 particles into fresh tubes, each containing a 500 µl solution of "$W_1$," which is a mixture of 2.6M GTC and 7.1M acetamide. Withdraw the magnets from the plastic sleeves, and then resuspend the sample 1-12 particles by mixing the sleeve with the $W_1$ solution. Reinsert the magnetic bar into the plastic sleeves for a total of 30 seconds, and then remove the sleeve/magnetic bar with the collected MAGAZORB™ paramagnetic particles.
9. Repeat step 7 two more times for a total of three washes with 500 µl of $W_1$ for each sample.
10. For each of samples 1 and 2, repeat step 7 an additional four times using $W_1$ for a total of seven washes with $W_1$.
11. For each of samples 3 and 4, repeat step 7 an additional four times using 500 µl of MAGAZORB™ DNA Binding Solution instead of $W_1$.
12. For each of samples 5 and 6, repeat step 7 an additional four times using 500 µl of Alcohol Wash, Blood (BW wash) (available from Promega, catalog item MB1001) solution instead of $W_1$.
13. Place the sleeve/magnetic bar and the collected sample 1-12 particles into fresh tubes, respectively, each containing 40 µl of WIZARD™ Genomic DNA Rehydration Solution (available from Promega, catalog item A7963). Withdraw the magnets from the plastic sleeves, and then resuspend the sample 1-12 particles by mixing the sleeve with the WIZARD™ Genomic DNA Rehydration Solution.
14. To each of samples 2 and 4, add 0.3 µl of 100 bp DNA (to highlight the 100 bp band in the sample).
15. To each of samples 6 and 8, add 0.3 µl of 200 bp DNA (to highlight the 200 bp band in the sample).
16. To each of samples 10 and 12, add 0.3 µl of 300 bp DNA (to highlight the 300 bp band in the sample).
17. To each of samples 4, 5, 7, 8, 11, and 12, add 4 µl of 300 bp DNA (to highlight the 300 bp band in the sample).
18. Using blue/orange 6× loading dye, load 8 µl of each of samples 1-12 into a respective one of twelve agarose gel electrophoresis lanes containing a 15% TBE-urea gel.
19. Perform electrophoresis using bromphenol blue dye at 120 volts for about 3 hours or until the bromphenol blue dye reaches the bottom slit of the gel. Stain each lane for 15 minutes with SYBR™ Gold, and digitally image all of the lanes using an ALPHA INNOTECH FLUORO-CHEM™ Imaging System, and, in particular, the Amersham TYPHOON™ platform with settings of: 1. ex488/em526. 2. PMT 450.

Figure 4:
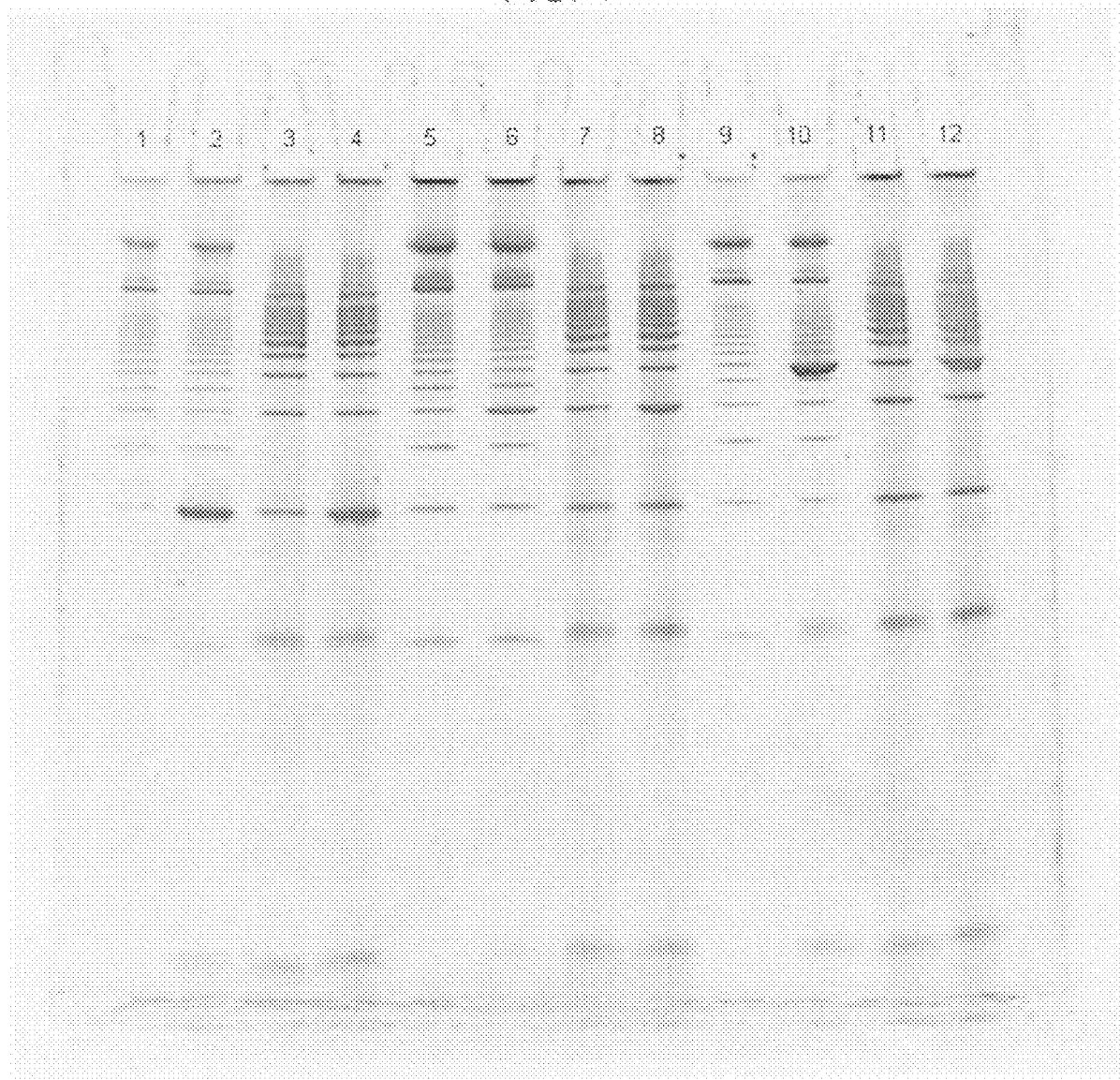
FIG. 4 is a photograph showing the results of an electrophoresis analysis performed in accordance with Example 6, described below.

FIG. 4 shows the results of the electrophoresis analysis of the twelve samples prepared according to Example 6. In FIG. 4, the lanes are numbered 1-12, from left to right. Lanes 1-12 show the results for samples 1-12, respectively.

As shown in FIG. 4, the GTC-A formulation in conjunction with a binding matrix is suitable in purifying genomic DNA that is anywhere from 25 bases to 20 kilobase pairs or larger. Specifically, lanes 2 and 10 show the purification of DNA which was about 25 bases in length and showed that oligo primers of 22 and 29 bases migrated to the bottom of the gel. Using BW wash (lanes 5 and 6) resulted in the purification of larger-sized DNA, about 75 bp, than the 25 bp obtained without using the BW wash. Furthermore, there are DNA bands in all three purification methods which can be seen, for example, between the 100 bp band and 200 bp band, as well as between the 200 bp and 300 bp bands, as a result of the added DNA bands being bound by the GTC-A formulation.

Example 7

In this example, nucleic acids from tissue culture cells were purified using a GTC-A formulation. The following procedure was used:
1. Prepare six samples, 1-6, by adding 600 µl of a mixture of 4.0M GTC, 5.0M acetamide, 20% (volume/volume) 1-thio-glycerol, 0.64% (weight/volume) CHAPS, 0.64% (volume/volume) TERGITOL™ type NP-9, and 0.16% (volume/volume) TRITON™ X-100 to each of six 1.5 ml plastic tubes.
2. To each of samples 1 and 2, add 200 µl of HeLa cells ($2 \times 10^6$ cells) and mix the samples by pipetting.
3. To sample 3, add 100 µl of HeLa cells in GIBCO™ DMEM medium ($1 \times 10^6$ cells) (available from INVITROGEN™, catalog item 11965092) and mix the sample by pipetting.
4. To each of samples 4 and 5, add 150 µl of Chinese Hamster Ovary (CHO) cells ($2 \times 10^6$ cells) and mix the sample by pipetting.
5. To sample 6, add 75 µl of CHO cells in GIBCO™ F-12 plus 10% FBS medium) ($1 \times 10^6$ cells) and mix the sample by pipetting.
6. Incubate each of samples 1-6 for 10 minutes at a temperature of about 21° C. and then place the samples into a respective one of six DNA IQ™ spin basket tubes, each containing a cellulose membrane column.
7. After allowing samples 1-6 to sit for five minutes at about 21° C., centrifuge the samples for one minute at 12,000×g (times gravity).
8. Remove the columns from each tube and then place the sample 1-6 columns into a respective clean 1.5 ml tube. To each of samples 1-6, add a mixture of 500 µl of 4.0M GTC, 5.0M acetamide, and 20% (volume/volume) 1-TG, and then centrifuge each sample for one minute at 12,000×g.
9. Repeat step 8 a second time.
10. Repeat step 8 two more times, except substituting a 500 µl mixture of 2.6M GTC and 7.1M acetamide for the 500 µl mixture of 4.0M GTC, 5.0M acetamide, and 20% (volume/volume) 1-TG used in step 8.
11. For samples 2 and 5 only, repeat step 8 one more time, except substituting 500 µl of SV Total RNA Wash for the 500 µl mixture of 4.0M GTC, 5.0M acetamide, and 20% (volume/volume) 1-TG used in step 8.
12. Place each of samples 1-6 into respective clean 1.5 ml tubes and add 50 µl of nuclease-free water to each tube.
13. Allow samples 1-6 to sit for two minutes at about 21° C., and then centrifuge the samples at 12,000×g for one minute. Elute the samples in nuclease-free water in order to reduce the amount of GTC-A carried over from the previous washes.
14. To maximize the nucleic acid yield, prepare six additional samples, 7-12, by removing the columns from samples 1-6 and placing them into respective clean 1.5 ml tubes.
15. Add 100 µl of nuclease-free water to each of samples 7-12, and then incubate the samples at about 56° C. for 15 minutes.
16. Centrifuge samples 7-12 at 12,000×g for one minute. Elute the samples in nuclease-free water.
17. Add 2 µl of 100 bp DNA ladder to sample 1 (to provide molecular weight reference marker, thus serving as a control).
18. Using blue/orange 6× loading dye, load 5 µl of each of samples 1-12 into a respective one of twelve agarose gel electrophoresis lanes containing a 10% TBE-urea gel (available from INVITROGEN™, Carlsbad, Calif., catalog item EC68752BOX).
17. Perform electrophoresis using bromphenol blue dye at 120 volts for about 3 hours or until the bromphenol blue dye reaches the bottom slit of the gel. Stain each lane for 15 minutes with SYBR™ Gold, and digitally image all of the lanes using an ALPHA INNOTECH FLUOROCHEM™ Imaging System, and, in particular, the Amersham TYPHOON™ platform with settings of: 1. ex488/em526. 2. PMT 450.

Figure 5:
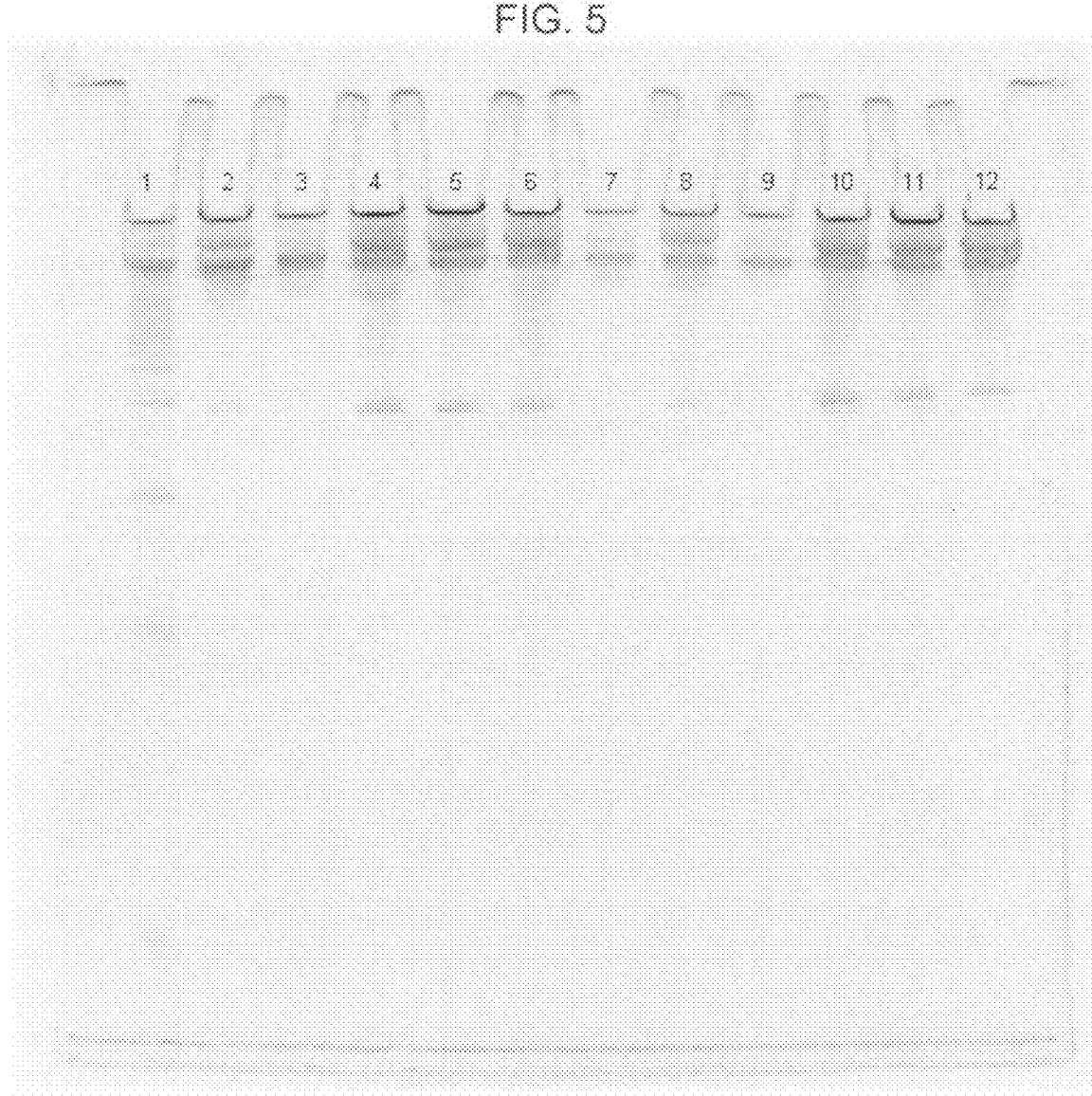
FIG. 5 is a photograph showing the results of an electrophoresis analysis performed in accordance with Example 7, described below.

FIG. 5 shows the results of the electrophoresis analysis of the samples prepared according to Example 7. In FIG. 5, the lanes are numbered 1-12, from left to right. Lane 1 shows the results for sample 1; lane 2 shows the results for sample 2; lane 3 shows the results for sample 3; lane 4 shows the results for sample 7; lane 5 shows the results for sample 8; lane 6 shows the results for sample 9; lane 7 shows the results for sample 4; lane 8 shows the results for sample 5; lane 9 shows the results for sample 6; lane 10 shows the results for sample 10; lane 11 shows the results for sample 11; and lane 12 shows the results for sample 12.

As shown in FIG. 5, in the case of tissue culture cells, the use of the GTC-A formulation allowed the purification of genomic DNA and total RNA from each of the samples prepared according to Example 7.

Example 8

In this example, cytoplasmic RNA from tissue culture cell samples was purified using GTC-A formulations. The following procedure was used:
1. Grow Human Embryonic Kidney 293 (HEK293) tissue culture cells in GIBCO™ DMEM medium. Allow 4 ml of $5 \times 10^6$ HEK293 cells to settle at 1×g, and then remove the growth medium by pipetting, so that about $2 \times 10^7$ cells are contained in 50 µl. Next, place the 50 µl of cells into a 1.5 ml plastic tube and place on ice for 5 minutes.
2. Add 6 µl of RNASIN™ Plus (40 units per µl) (available from Promega, catalog item 1232) to the 50 µl of cells from step 1. Then add 100 µl of 120 µg/ml digitonin in 100 mM EDTA 100 mM HEPES™ (pH 7.5) (on ice) to the cells. Mix the contents by vortexing for 10 seconds, and then incubate on ice for 20 minutes. The incubation with 77 µg/ml digitonin promotes the lysis of the cytoplasmic membrane, without lysis of the cell nuclear membrane.
3. Centrifuge the suspension from step 2 at 13,000×g for five minutes at about 4° C. to pellet the nuclei and cellular debris.
4. Prepare four samples, 1-4, by dispensing 40 µl of the supernatant of the suspension from step 3 into 1.5 ml plastic tubes containing the following: (a) for each of samples 1 and 2, 400 µl of a mixture of 4.0M GTC, 5.0M acetamide, 20% (volume/volume) 1-TG, and 10 µl of MAGAZORB™ paramagnetic particles; and (b) for each of samples 3 and 4, a DNA-IQ™ column and 400 µl of a mixture of 4.0M GTC, 5.0M acetamide, and 20% (volume/volume) 1-TG.
5. Mix each of samples 3 and 4 by pipetting, allow them to settle for 20 seconds at a temperature of about 21° C., and then spin samples 3 and 4 at 13,000×g for one minute. Remove the column flowthrough of samples 3 and 4 and place them into fresh 1.5 ml tubes. Then, add 10 µl of MAGNESIL™ Blue to the column flowthrough of samples 3 and 4.
6. Mix the four samples from step 5 by pipetting and incubating them at about 21° C. for five minutes. Place each of samples 1-4 on a magnetic. After separation of the particles from the samples, discard the supernatants from the particles that are attracted to the side of the tubes.
7. Wash the remaining particles of each of samples 1-4 with 400 µl of a mixture of 4.0M GTC, 5.0M acetamide, and 20% (volume/volume) 1-TG.
8. Place the samples containing magnetic particles on magnetic stands, magnetize, and discard the supernatants from the particles that are attracted to the side of the tubes.
9. Transfer the DNA-IQ™ columns from step 5 to clean 1.5 ml tubes. Wash the columns using 400 µl of SV RNA Wash Solution. Repeat this wash process an additional time for samples 2-4.
10. Place all four samples containing paramagnetic particles on a magnetic stand, discard the supernatants, and allow the samples to air dry for 10 minutes.
11. Place the DNA-IQ™ columns into clean 1.5 ml tubes and number these as samples 5 and 6.
12. Elute each of samples 1-6 with 40 µl of nuclease-free water per sample for 10 minutes at a temperature of about 21° C. Place the samples containing paramagnetic particles on a magnetic rack.
13. Using blue/orange 6× loading dye, load 10 µl of sample from each tube into separate agarose gel electrophoresis lanes containing a 15% TBE-urea gel.
14. Perform electrophoresis using bromphenol blue dye at 120 volts for about 3 hours or until the bromphenol blue dye reaches the bottom slit of the gel. Stain each lane for 15 minutes with SYBR™ Gold, and digitally image all of the lanes using an ALPHA INNOTECH FLUORO-CHEM™ Imaging System, and, in particular, the Amersham TYPHOON™ platform with settings of: 1. ex488/em526. 2. PMT 450.

FIG. 6 shows the results of the electrophoresis analysis of the samples prepared according to Example 8. Lane 1 shows a 100 bp DNA ladder for the purpose of comparing a DNA sequence; lane 2 shows the results of 10 µl of initial cytoplasmic RNA supernatant to serve as a marker of non purified nucleic acid; lane 3 shows the results for sample 3; lane 4 shows the results for sample 4; lane 5 shows the results for sample 1; lane 6 shows the results for sample 2; lane 7 shows the results for sample 5; lane 8 shows the results for sample 6; lane 9 shows 100 bp DNA ladder for the purpose of comparing a DNA sequence; lane 10 shows the results for sample 7; lane 11 shows the results for sample 8; and lane 12 is empty.

As demonstrated in FIG. 6, RNA is purified using the GTC-acetamide formulation and SV RNA Wash, using either MAGAZORB™ paramagnetic cellulose particles or MAGNESIL™ paramagnetic silica particles. In addition, ribosomal RNA and tRNA bands are visible in lanes 7 and 8, showing purification using GTC-A. Furthermore, the passage of the cytoplasmic RNA sample through a cellulose column (lanes 3 and 4), with a short sample incubation time of 20 seconds at a temperature of about 21° C., substantially removed nuclear DNA. This was accomplished without substantial removal of the cytoplasmic RNA, demonstrated by the subsequent purification using MAGNESIL™ particles (lanes 10 and 11).

Example 9

In this example, DNA or RNA from tissue culture cell samples was purified using a GTC-A formulation with the aid of various binding matrices in order to determine additional binding matrices suitable for use with the present invention. The following procedure was used:
1. Centrifuge $2.3 \times 10^7$ HEK293 cells, grown in DMEM medium, at 1000×g in a 50 ml plastic tube for five minutes. Decant the supernatant and mix the pelleted cells by vortexing.
2. In order to lyse the HEK293 cells, add 8 ml of a mixture of 4.0M GTC, 5.0M acetamide, 20% (volume/volume) 1-TG, 0.64% (weight/volume) CHAPS, 0.64% (volume/volume) TERGITOL™ type NP-9, and 0.16% (volume/volume) TRITON™ X-100. Mix the lysate by vortexing until a uniform mixture is obtained.
3. Prepare twenty-four samples, 1-24, by adding the indicated one of the following binding matrices to a 1.5 ml plastic tube: (a) for samples 1 and 2, a cellulose membrane in a DNA-IQ™ column; (b) for samples 3 and 4, a silica membrane in a SV column; (c) for samples 5 and 6, a cellulose acetate membrane in a CORNING™ spin column; (d) for samples 7 and 8, a nylon membrane in a CORNING™ spin column; (e) for samples 9 and 10, a PVDF membrane in a polypropylene spin column; (f) for samples 11 and 12, a polypropylene membrane in a DNA-IQ™ column; (g) for samples 13 and 14, a HIGH PURE™ Spin Filter tube; (h) for samples 15 and 16, a clearing column; (i) for samples 17 and 18, 10 µl (3.4 mg) of paramagnetic zeolite particles; (j) for samples 19 and 20, 20 µl (1 mg) of MAGAZORB™ paramagnetic particles; (k) for samples 21 and 22, 10 µl (1 mg) of MAGNESIL™ Blue; and (l) for samples 23 and 24, 50 µl (5 mg) of DNA-IQ™ paramagnetic particles.
4. Add 300 µl of HEK293 lysate to each of samples 1-24.
5. Incubate all of samples 1-24 at about 21° C. for 10 minutes. Then place samples 17-24, which contain particles, on a magnetic rack in order to separate the particles from the supernatants. Then discard the supernatants.
6. Centrifuge column samples 1-16 at 13,000×g for five minutes. Note that the PVDF columns (samples 9 and 10) allow only about half of the solution to flow through the membrane. Thus, the unprocessed fluid is to be discarded along with the flowthroughs.
7. Resuspend each of particle samples 17-24 in 400 µl of a mixture of 1.7M GTC and 7.5M acetamide by pipetting, and then place the particle samples back on the magnetic rack. Discard the supernatants.
8. Repeat step 7 three more times using 400 µl of SV RNA Wash Solution instead of the GTC-A formulation. After discarding the third RNA wash solution, air-dry the particle samples for 20 minutes at a temperature of about 21° C. Then elute the nucleic acids in 40 µl of nuclease-free water.
9. Wash each of column samples 1-16 with a 400 µl mixture of 1.7M GTC and 7.5M acetamide, followed by centrifugation at 13,000×g for five minutes. Discard the column flowthroughs.
10. Wash each of column samples 1-16 twice with 400 µl of SV RNA Wash Solution, followed by centrifugation at 13,000×g for five minutes, and then discard the column flowthroughs. Then, spin the column samples at 13,000×g for one minute to ensure the columns are dry, and then elute each column sample with 40 µl of nuclease-free water.

11. Store all of samples 1-24 at about −20° C. for 16 hours.
13. After magnetic separation of samples 17-24, load 10 µl of each sample into a respective one of twenty-four agarose gel electrophoresis lanes containing a 15% TBE-urea gel, using blue/orange 6× loading dye.
14. Perform electrophoresis using bromphenol blue dye at 120 volts for about 3 hours or until the bromphenol blue dye reaches the bottom slit of the gel. Stain each lane for 15 minutes with SYBR™ Gold, and digitally image all of the lanes using an ALPHA INNOTECH FLUORO-CHEM™ Imaging System, and, in particular, the Amersham TYPHOON™ platform with settings of: 1. ex488/em526. 2. PMT 450.

Figure 7A:
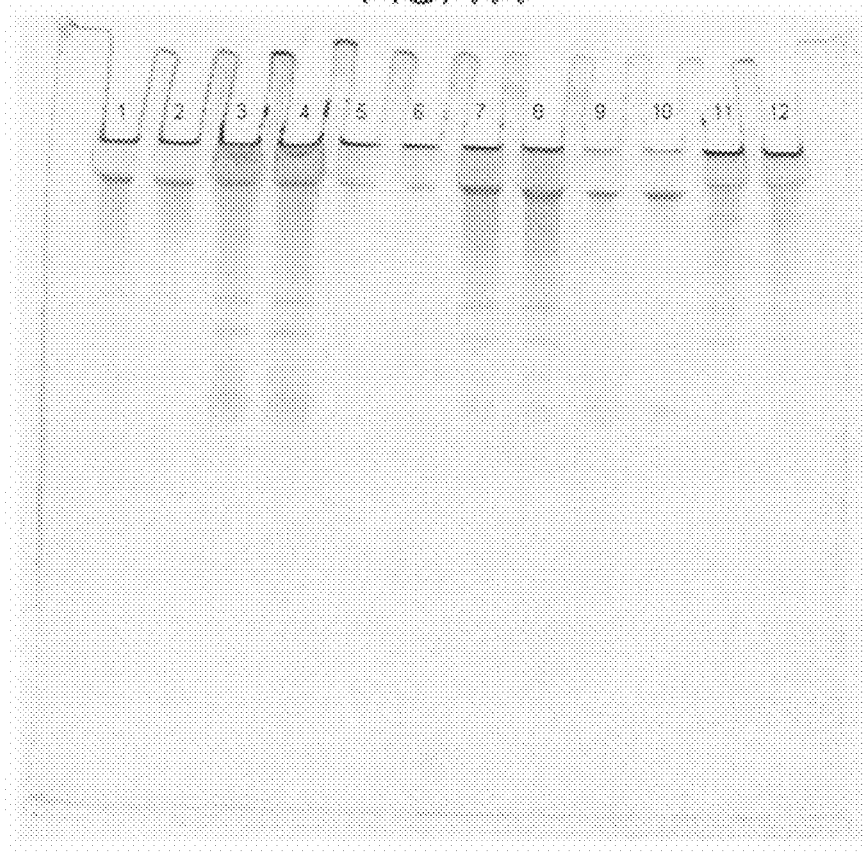
FIGS. 7A and 7B are photographs showing the results of an electrophoresis analysis performed in accordance with Example 9, described below.
Figure 7B:
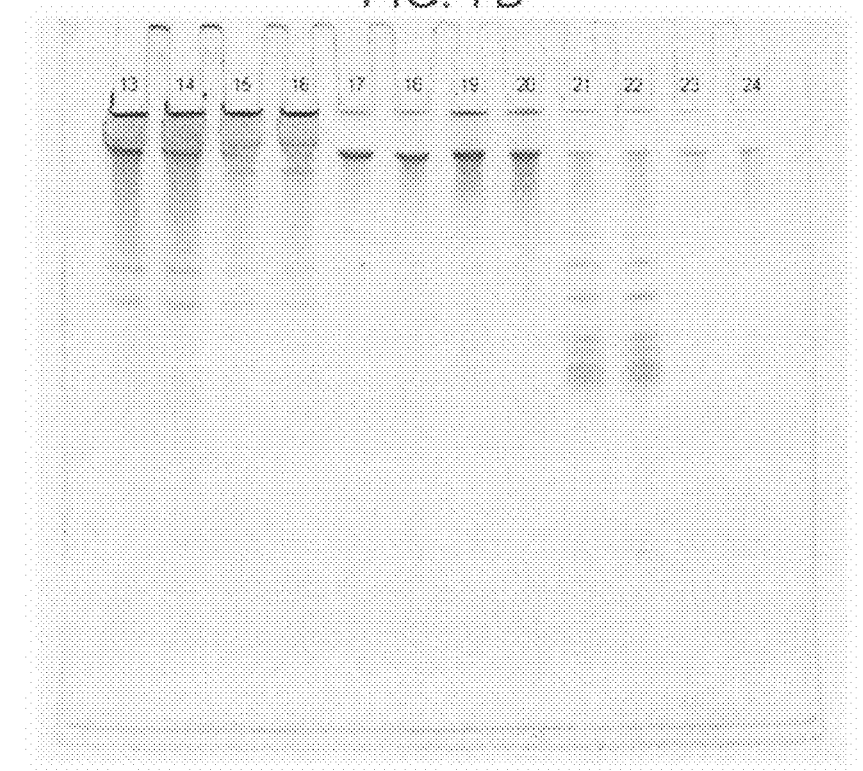

FIGS. 7A and 7B show the results of the electrophoresis analysis of the samples prepared according to Example 9. In FIG. 7A, the lanes are numbered 1-12, from left to right. In FIG. 7B, the lanes are numbered 13-24, from left to right. Lanes 1-24 show the results for samples 1-24, respectively.

As shown in FIGS. 7A and 7B, genomic DNA was purified using cellulose acetate columns, PVDF columns, DNA-IQ™ paramagnetic particles, and MAGNESIL™ Blue particles. In addition, MAGAZORB™ paramagnetic particles purified a small amount of RNA as well as genomic DNA. Both RNA and DNA were purified using SV silica columns, nylon membrane columns, polypropylene membrane columns, HIGH PURE™ Spin columns, clearing columns, and paramagnetic zeolite particles, which showed prominent tRNA bands.

Furthermore, this example shows how to screen for the initial binding of nucleic acids to a binding matrix, followed by the retention of nucleic acids during sequential washes, and elution of the nucleic acids at the end of the procedure. For example previous examples have shown binding of both DNA and RNA to MAGAZORB™ paramagnetic particles, and in this example (with washes using SV RNA Wash) the RNA was less prominent in the elution. Therefore, in order to screen binding matrices for binding of nucleic acids, one could wash only with the initial GTC-A formulation to ensure retention of nucleic acids on the binding matrix. This example demonstrated a measure of the ability to retain the nucleic acids on the binding matrix during wash steps. Additionally, this example also required that the nucleic acid was eluted from the binding matrix. In addition to the requirement that the binding matrix has bound DNA or RNA, the nucleic acid must also remain bound during washes with two different solutions, and also allows the nucleic acid to elute from the binding matrix at the end of the purification. Even with all three requirements, it is shown that all of the binding matrices show an ability to purify nucleic acid(s) using GTC-A formulations.

Example 10

In this example, DNA and RNA from the same tissue culture cell samples were purified using a GTC-A formulation. The following procedure was used:
1. Centrifuge $1.6 \times 10^7$ HEK293 cells grown in DMEM medium at 1000×g in a 15 ml plastic tube for five minutes.
2. Lyse the cells adding 6 ml of $D_X$. Then mix the lysate by repeated pipetting until a uniform mixture is obtained.
3. Prepare two samples, 1 and 2, by adding 400 µl of the lysate from step 2 to each of two 1.5 ml plastic tubes, each containing 50 µl (5 mg) of DNA-IQ™ particles. Mix the samples, and then incubate for 10 minutes at about 21° C.
4. Magnetize the particles in each of samples 1 and 2 using a magnetic rack.
5. Prepare two additional samples, 3 and 4, by transferring the supernatants from samples 1 and 2, respectively, to clean tubes, each containing 10 µl (3.4 mg) of paramagnetic zeolite particles. Samples 1 and 2 now consist of the DNA-IQ™ particles minus the supernatants.
6. Mix and incubate each of samples 3 and 4 for 10 minutes at a temperature of about 21° C. Next, magnetize the particles in each of samples 3 and 4 using a magnetic rack and remove the supernatants from each of samples 3 and 4.
7. Wash each of samples 1-4 with 800 µl of a mixture of 4.0M GTC, 5.0M acetamide, and 20% (volume/volume) 1-TG. Then wash each of the samples an additional three times with 800 µl of SV RNA Wash Solution.
8. Magnetize the particles in samples 1-4, remove the supernatants, and then air dry the particles for 20 minutes at a temperature of about 21° C.
9. Elute the particles in each of samples 1-4 in 40 µl of nuclease-free water for ten minutes at a temperature of about 21° C. in order to allow the nucleic acids to elute from the particles.
10. Using blue/orange 6× loading dye, load 10 µl of each of samples 1-4 into a respective one of four agarose gel electrophoresis lanes containing a 15% TBE-urea gel.
11. Perform electrophoresis using bromphenol blue dye at 120 volts for about 3 hours or until the bromphenol blue dye reaches the bottom slit of the gel. Stain each lane for 15 minutes with SYBR™ Gold, and digitally image all of the lanes using an ALPHA INNOTECH FLUORO-CHEM™ Imaging System, and, in particular, the Amersham TYPHOON™ platform with settings of: 1. ex488/em526. 2. PMT 450.

Figure 8:
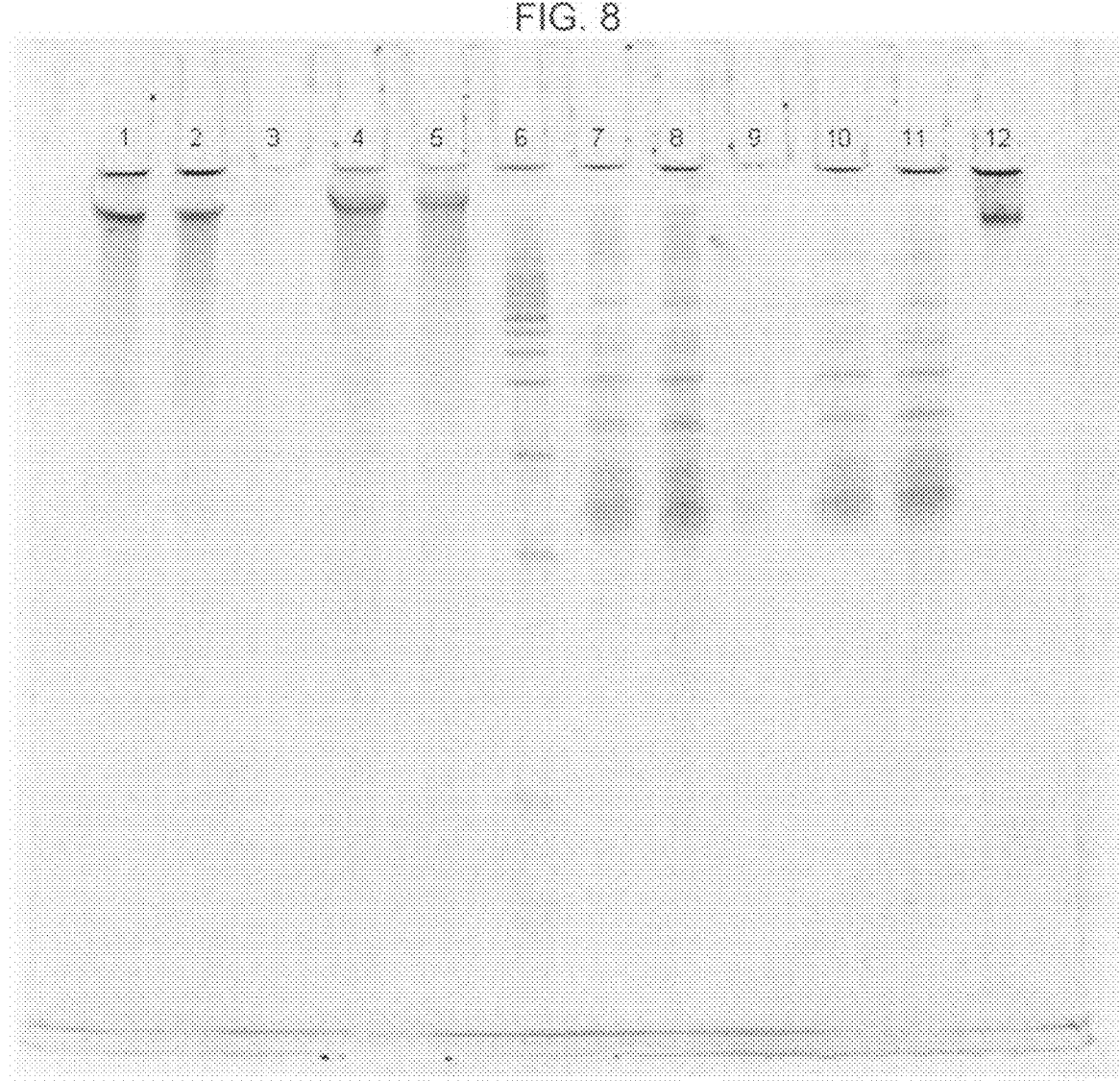
FIG. 8 is a photograph showing the results of an electrophoresis analysis performed in accordance with Example 10, described below.

FIG. 8 shows the results of an agarose gel electrophoresis analysis of the samples prepared according to Example 10. In FIG. 8, the lanes are numbered 1-12, from left to right. Lanes 1 and 2 show the results for samples 1 and 2, respectively; lane 3 is blank; lanes 4 and 5 show samples 1 and 2, respectively, digested with RNase ONE lane 6 contains Promega 100 bp DNA ladder; lanes 7 and 8 show results for samples 3 and 4, respectively; lane 9 is blank; lanes 10 and 11 show samples 3 and 4, respectively, digested with Promega RQ1 RNase-free DNase; and lane 12 contains Promega genomic DNA.

As shown in FIG. 8, genomic DNA was purified using DNA-IQ™ particles, and from the same medium, RNA was purified using paramagnetic zeolite particles. Thus, DNA and RNA can be purified from the same medium using a first binding matrix to bind DNA and a second binding matrix to bind RNA, without adding any additional solution or condition between the first binding matrix and the application of the second binding matrix.

Example 11

In this example, RNA from tissue culture cell mediums were purified using GTC-A formulations containing GTC and acetamide, N-methylacetamide or N,N-dimethylacetamide. The following procedure was used:
1. Allow 25 ml of $1.5 \times 10^6$ HEK293 tissue culture cells, grown in GIBCO™ DMEM medium, to settle at 1×g for sixty minutes at about 21° C., and then remove the growth medium supernatant by pipetting, so that about $3.7 \times 10^7$ cells are contained in 1.5 ml (about $2.5 \times 10^6$ cells per 100 µl).
2. Prepare twelve samples, 1-12, by adding the following to a respective one of twelve 1.5 ml plastic tubes: (a) for samples 1-6, 100 µl of HEK293 tissue culture cells; and (b) for samples 7-12, 100 µl of human whole blood.

3. To each of samples 2, 4, 6, 8, 10, and 12, add 10 µl of Promega 100 base pair ladder.
4. To each sample, add the indicated GTC-A formulation: (a) for each of samples 1, 2, 7, and 8, 300 µl of a mixture of 4.0M GTC, 5.0M acetamide, and 20% (volume/volume) 1-TG; (b) for each of samples 3, 4, 9, and 10, 500 µl of a mixture of 4.0M GTC, 5.0M N-methylacetamide, and 10% (volume/volume) 1-TG; and (c) for each of samples 5, 6, 11, and 12, 500 µl of a mixture of 4.0M GTC, 5.0M N,N-dimethylacetamide, and 10% (volume/volume) 1-TG.
5. Mix each of samples 1-12 by vortexing, and then incubate the samples for five minutes at about 21° C.
6. Transfer each of samples 1-12 to one a respective 1.5 ml plastic tube containing DNA-IQ™ cellulose mini-columns, and then centrifuge the samples at 11,000×g for two minutes.
7. Transfer each of samples 1-12 DNA-IQ™ cellulose mini-columns to fresh 1.5 ml tubes, then wash each mini-column with 500 µl of the same GTC-A formulation used in step 4.
8. Elute each of samples 1-12 with 40 µl of nuclease-free water and then remove the mini-columns
9. Prepare twelve additional samples, 13-24, by placing the mini-columns removed from samples 1-12, respectively, into fresh 1.5 ml tubes.
10. Elute each of samples 13-24 with 40 µl of nuclease-free water and then discard the mini-columns
11. Using blue/orange 6× loading dye, load 10 µl of each of samples 1-24 into a respective one of twenty-four agarose gel electrophoresis lanes containing a 15% TBE-urea gel.
12. Perform electrophoresis using bromphenol blue dye at 120 volts for about 3 hours or until the bromphenol blue dye reaches the bottom slit of the gel. Stain each lane for 15 minutes with SYBR™ Gold, and digitally image all of the lanes using an ALPHA INNOTECH FLUORO-CHEM™ Imaging System, and, in particular, the Amersham TYPHOON™ platform with settings of: 1. ex488/em526. 2. PMT 450.

Figure 9A:
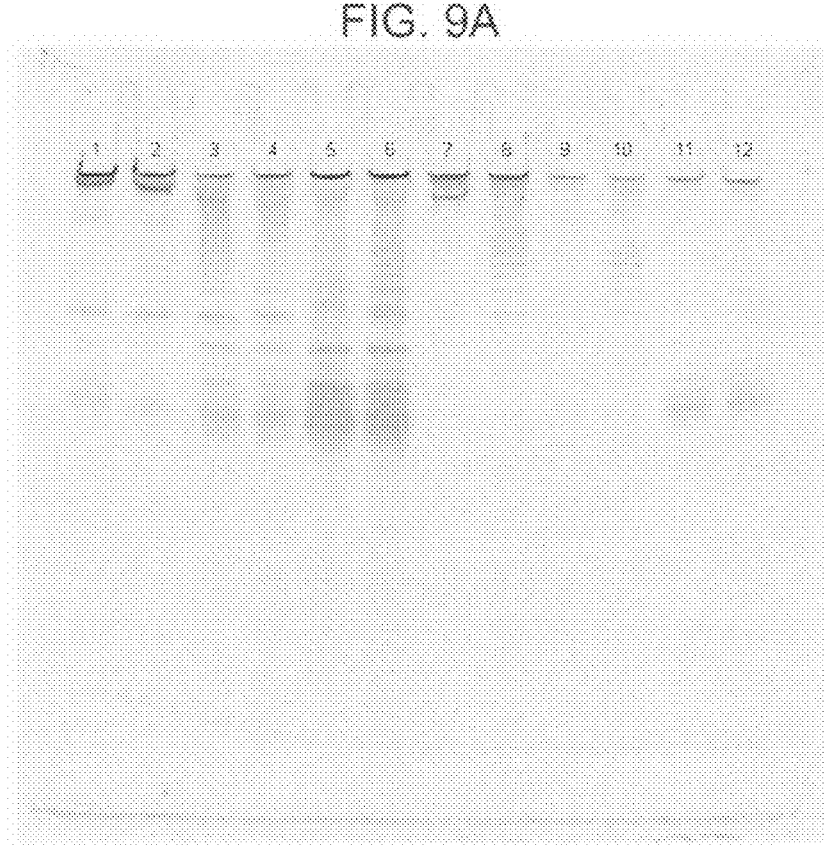
FIGS. 9A and 9B are photographs showing the results of an electrophoresis analysis performed in accordance with Example 11, described below.
Figure 9B:
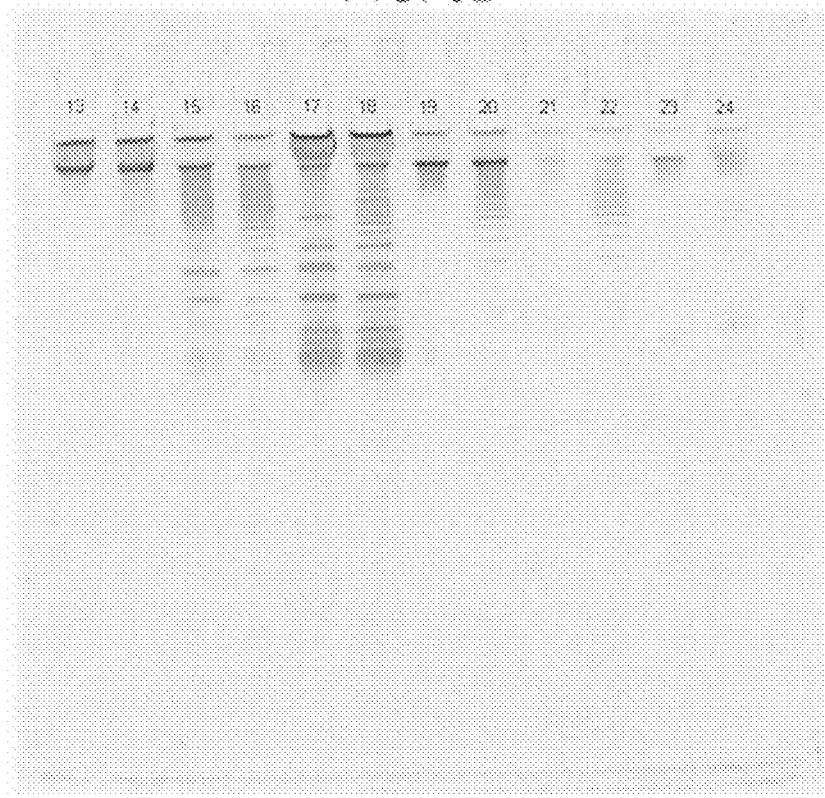

FIGS. 9A and 9B show the results of the electrophoresis analysis of the samples prepared according to Example 11. In FIG. 9A, the lanes are numbered 1-12, from left to right. In FIG. 9B, the lanes are numbered 13-24, from left to right. Lanes 1-24 show the results for samples 1-24, respectively.

As shown in FIGS. 9A and 9B, DNA and RNA are bound to cellulose membranes in mini-columns, and purified using GTC and acetamide, GTC and N-methylacetamide, and GTC and N,N-dimethylacetamide, showing that derivatives of acetamide can also be used in conjunction with GTC to purify nucleic acids.

Example 12

In this example, DNA purified from human whole blood was bound to a blood card, which served as a binding matrix. Additionally, the blood sample can be washed on the blood card, and purified nucleic acids can be obtained by elution of blood card punches. The following procedure was used:
1. Prepare two samples, 1 and 2, by adding 200 µl of a mixture of 4.0M GTC, 5.0M acetamide, 20% (volume/volume) 1-TG, 0.64% (weight/volume) CHAPS, 0.64% (volume/volume) TERGITOL™ type NP-9, and 0.16% (volume/volume) TRITON™ X-100 to each of two 1.5 ml plastic tubes.
2. Add 100 µl of human whole blood to each of samples 1 and 2.
3. To sample 2, add 10 µl of Promega 100 bp ladder.
4. Mix each of samples 1 and 2 thoroughly by pipetting at a temperature of about 21° C.
5. In 10 µl increments, spot each of samples 1 and 2 onto a Schleicher & Schuell cellulose card, with successive additions being applied only after the previous addition has been absorbed by the cellulose card. Continue until the entire sample (300 µl for sample 1 and 310 µl for sample 2) has been applied to the cellulose card.
6. Spot 100 µl of human whole blood plus 10 µl of RNA Marker (available from Promega, catalog item G3191) onto the cellulose card in order to compare the nucleic acids.
7. To the sample 2 spot, apply 150 µl of a mixture of 2.6M GTC and 7.1M acetamide in 10 µl increments, with successive additions being applied only after the previous addition has been absorbed by the cellulose card. The resulting blood spot should have a relatively white center, and a concentric red circle containing hemoglobin and other cellular debris.
8. Take a central punch of about 2 mm×2 mm from the center of each of the sample 1 and 2 spots, and then take a second punch of about 2 mm×2 mm from about 5 mm outside of each center.
9. Elute each the four punches in 20 µl of nuclease-free water.
10. Using blue/orange 6× loading dye, load 10 µl of the elution from each of the four punches into a respective one of four agarose gel electrophoresis lanes containing a 15% TBE-urea gel.
11. Perform electrophoresis using bromphenol blue dye at 120 volts for about 3 hours or until the bromphenol blue dye reaches the bottom slit of the gel. Stain each lane for 15 minutes with SYBR™ Gold, and digitally image all of the lanes using an ALPHA INNOTECH FLUORO-CHEM™ Imaging System, and, in particular, the Amersham TYPHOON™ platform with settings of: 1. ex488/em526. 2. PMT 450.

Figure 10:
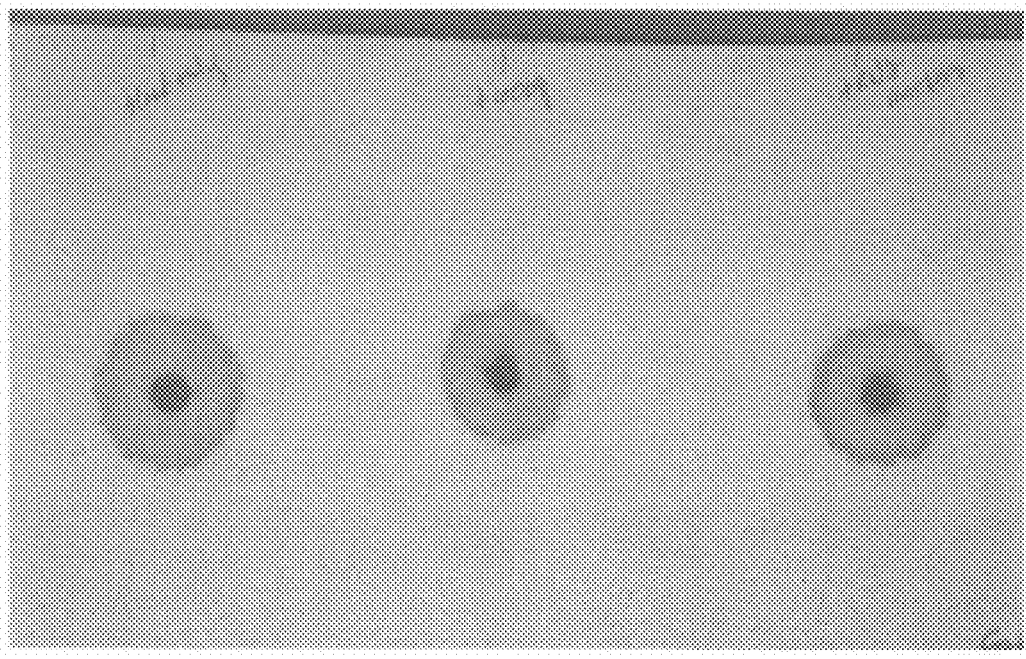
FIG. 10 is a photograph showing the results of a blood card prepared in accordance with Example 12, described below.

FIG. 10 shows the Schleicher & Schuell cellulose card prepared according to Example 12. The spot on the left corresponds to sample 1; the spot in the middle corresponds to sample 2; and the spot on the right corresponds to the blood plus RNA Marker.

Figure 11:
FIG. 11 is a photograph showing the results of an electrophoresis analysis performed in accordance with Example 12, described below.

FIG. 11 shows the results of the electrophoresis analysis of the four elutions prepared according to Example 12. In FIG. 11, the lanes are numbered 1-12, from left to right. Lane 1 shows the results for the center punch of sample 1; lane 3 shows the results for the second punch of sample 1; lane 5 shows the results for the center punch of sample 2; lane 7 shows the results for the second punch of sample 2; lane 9 shows Promega 100 bp DNA Ladder; lane 11 shows Promega genomic DNA standard; and the remaining lanes are empty.

As shown in FIG. 11, substantially more DNA was obtained from the center punches than from the second punches for each of samples 1 and 2. Furthermore, DNA of sizes down to 50 base pairs can be retained in the central blood application spot and be eluted with nuclease-free water.

Although this invention has been described in certain specific exemplary embodiments, many additional modifications and variations would be apparent to those skilled in the art in light of this disclosure. It is, therefore, to be understood that this invention may be practiced otherwise than as specifically described. Thus, the exemplary embodiments of the invention should be considered in all respects to be illustrative and not restrictive, and the scope of the invention to be determined by any claims supported by this application, and the equivalents thereof, rather than by the foregoing description.

I claim:

1. A method of purifying a nucleic acid present in an in vivo cellular environment, the nucleic acid and in vivo cellular environment being contained in a medium, the method comprising:
   (a) combining a medium containing a nucleic acid a binding matrix and a formulation, the formulation comprising:
      i) guanidine thiocyanate; and
      ii) acetamide, or one or more acetamide derivatives, or a combination of acetamide and one or more acetamide derivatives, the amounts of the guanidine thiocyanate and the acetamide, the acetamide derivative(s), or the combination of acetamide and acetamide derivative(s) present in the formulation being sufficient to cause the nucleic acid to separate from its in vivo cellular environment and bind to the binding matrix;
   (b) separating the binding matrix with the nucleic acid bound thereto from substantially the rest of the combined medium and formulation; and
   (c) eluting the nucleic acid from the binding matrix, thereby obtaining the nucleic acid in a substantially purified form wherein said acetamide derivatives are N-methylacetamide and N,N-dimethylacetamide.

2. The method of claim 1, wherein the concentration of the guanidine thiocyanate in the formulation is from approximately 1.7M to approximately 4.3M, and the concentration of the acetamide, the acetamide derivative(s), or the combination of acetamide and acetamide derivative(s) in the formulation is from approximately 5.0M to approximately 7.5M.

3. The method of claim 1, wherein a second nucleic acid is present in the medium and a second binding matrix is provided in step (a), wherein the binding matrix is capable of binding the nucleic acid and the second binding matrix is capable of binding the second nucleic acid.

4. The method of claim 1, wherein the binding matrix comprises one or more materials selected from the group consisting of paramagnetic cellulose particles, paramagnetic carboxy-cellulose particles, paramagnetic citrus pectin particles, paramagnetic apple pectin particles, paramagnetic zeolite particles, paramagnetic silica particles, cellulose membranes, silica membranes, cellulose acetate columns, nylon membrane columns, PVDF membrane columns, polypropylene columns, and clearing columns.

5. The method of claim 1, wherein step (a) further comprises combining one or more additional ingredients with the medium, the binding matrix, and the formulation, the one or more additional ingredients being selected from the group consisting of proteinase K, beta-mercaptoethanol, tris(carboxyethyl)phosphine, dithiothreitol, 1-thioglycerol, digitonin, lysis solutions, 3-[(3-cholamidopropyl)dimethylammonio]-1-propanesulfonate, 26-(4-nonylphenoxy)-3,6,9,12,15,18,21,24-octaoxahexacosan-1-ol, and 4-(1,1,3,3-tetramethylbutyl)phenyl-polyethylene glycol.

6. A method of binding a nucleic acid present in an in vivo cellular environment, the nucleic acid and in vivo cellular environment being contained in a medium, to a binding matrix, the method comprising combining a medium containing the nucleic acid with the binding matrix and a formulation, the formulation comprising
   (a) guanidine thiocyanate; and
   (b) acetamide, or one or more acetamide derivatives, or a combination of acetamide and one or more acetamide derivative(s); the amounts of the guanidine thiocyanate, the acetamide, the acetamide derivative(s), or the combination of acetamide and acetamide derivative(s) present in the formulation being sufficient to cause the nucleic acid to separate from its in vivo cellular environment and bind to the binding matrix wherein said acetamide derivatives are N-methylacetamide and N,N-dimethylacetamide.

7. The method of claim 6, wherein the concentration of the guanidine thiocyanate in the formulation is from approximately 1.7M to approximately 4.3M, and the concentration of the acetamide, the acetamide derivative(s), or the combination of acetamide and acetamide derivative(s) in the formulation is from approximately 5.0M to approximately 7.5M.

8. The method of claim 7, wherein the concentration of the guanidine thiocyanate in the formulation is from approximately 4.0M to approximately 4.3M, and the concentration of the acetamide, the acetamide derivative(s), or the combination of acetamide and acetamide derivative(s) in the formulation is from approximately 5.0M to approximately 7.1M.

9. The method of claim 6, wherein the ratio of the formulation to the medium is from 1:1 to 30:1, by volume, and the ratio of the binding matrix to the medium is from 0.005:1 to 0.5:1, by volume.

10. The method of claim 9, wherein the ratio of the formulation to the medium is from 1.5:1 to 8:1, by volume, and the ratio of the binding matrix to the medium is from 0.2:1 to 0.4:1, by volume.

11. The method of claim 7, wherein the binding matrix comprises one or more materials selected from the group consisting of paramagnetic cellulose particles, paramagnetic carboxy-cellulose particles, paramagnetic citrus pectin particles, paramagnetic apple pectin particles, paramagnetic zeolite particles, paramagnetic silica particles, cellulose membranes, silica membranes, cellulose acetate columns, nylon membrane columns, PVDF membrane columns, and polypropylene columns.

12. A kit comprising a binding matrix and a formulation, the formulation comprising an amount of guanidine thiocyanate and an amount of (i) acetamide, or (ii) one or more acetamide derivatives, or (iii) a combination of acetamide and one or more acetamide derivatives, the amounts of the guanidine thiocyanate and the acetamide, the acetamide derivative(s), or the combination of acetamide and acetamide derivative(s) present in the formulation being sufficient to cause a nucleic acid present in an in vivo cellular environment, the nucleic acid and in vivo cellular environment contained in a medium, to separate from its in vivo cellular environment and to bind to the binding matrix, when the medium containing the at least one nucleic acid is combined with the binding matrix and the formulation wherein said acetamide derivatives are N-methylacetamide and N,N-dimethylacetamide.

13. The kit of claim 12, wherein the concentration of the guanidine thiocyanate in the formulation is from approximately 1.7M to approximately 4.3M, and the concentration of the acetamide, acetamide derivative(s), or the combination of acetamide and acetamide derivative(s) in the formulation is from approximately 5.0M to approximately 7.5M.

14. The kit of claim 13, wherein the concentration of the guanidine thiocyanate in the formulation is from approximately 4.0M to approximately 4.3M, and the concentration of the acetamide, the acetamide derivative(s), or the combination of acetamide and acetamide derivative(s) in the formulation is from approximately 5.0M to approximately 7.1M.

15. The kit of claim 12, wherein the ratio of the binding matrix to the formulation in the kit is from 1:400 to 1:1, by volume.

* * * * *